(12) United States Patent
Cheng et al.

(10) Patent No.: US 9,713,873 B2
(45) Date of Patent: Jul. 25, 2017

(54) CONTINUUM STYLE MANIPULATOR ACTUATED WITH PHASE CHANGE MEDIA

(71) Applicant: MASSACHUSETTS INSTITUTE OF TECHNOLOGY, Cambridge, MA (US)

(72) Inventors: Nadia G. Cheng, Cambridge, MA (US); Maxim B. Labovsky, Cambridge, MA (US); Annette E. Hosoi, Cambridge, MA (US); Karl D. Iagnemma, Washington, DC (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 351 days.

(21) Appl. No.: 14/398,993

(22) PCT Filed: Mar. 12, 2013

(86) PCT No.: PCT/US2013/030354
§ 371 (c)(1),
(2) Date: Nov. 5, 2014

(87) PCT Pub. No.: WO2013/184192
PCT Pub. Date: Dec. 12, 2013

(65) Prior Publication Data
US 2015/0141756 A1 May 21, 2015

Related U.S. Application Data

(60) Provisional application No. 61/646,280, filed on May 12, 2012.

(51) Int. Cl.
*B65G 1/00* (2006.01)
*B25J 18/06* (2006.01)
(Continued)

(52) U.S. Cl.
CPC ............. *B25J 18/06* (2013.01); *A61B 1/0016* (2013.01); *A61B 1/0057* (2013.01);
(Continued)

(58) Field of Classification Search
CPC .......... B25J 18/06; A61B 34/70; A61B 34/71; A61B 1/00078; A61B 1/0016; A61B 1/0057
See application file for complete search history.

(56) References Cited

U.S. PATENT DOCUMENTS 3,497,083 A * 2/1970 Anderson ................... B25J 9/06
138/120
4,621,965 A * 11/1986 Wilcock .................... B25J 18/06
414/7
(Continued)

FOREIGN PATENT DOCUMENTS

EP          0249318 A1 * 12/1987 ............... B23Q 1/34
WO       2011130475      10/2011

OTHER PUBLICATIONS

The International Search Report and the Written Opinion of the International Search Authority, PCT/US2013/030,354, filed on Mar. 12, 2013, of which this case in the U.S. National Phase. The Search Report was mailed Dec. 9, 2013.
(Continued)

*Primary Examiner* — David M Fenstermacher
(74) *Attorney, Agent, or Firm* — Steven J. Weissburg, Esquire

(57) ABSTRACT

A continuum style manipulator is actuated by jammable media within an envelope of a module, which is also actuated by a tensile element, such as a cable and spooler motor. Multiple modules may be reversibly added. Two or more tensile elements may also be used. Three or more actuated tensile elements can actuate three DOFs of each module, and the terminal module, as well as the entire
(Continued)

manipulator. Jammable media may be granular, actuated by a pressure change. Coarsely ground coffee works well. Rather than a jammable media, tensile elements may alternatively be used with other phase change media, such as magnetorheological and electrorheological media. A high friction angle of the granular media is desirable, and has been achieved with a particle size dispersion including both small and relatively larger particles. Applications include endoscopes, proctoscopes, laparoscopic instruments, manufacturing and medical manipulators. Methods of actuating include unjamming all modules, positioning the manipulator with tensile elements or otherwise, jamming the base-most module, and then repositioning remaining, not-jammed modules, followed by jamming the base-most not-jammed module, and so on, until all modules are positioned and jammed.

34 Claims, 10 Drawing Sheets

(51) Int. Cl.
  *A61B 1/00* (2006.01)
  *A61B 1/005* (2006.01)
  *B25J 9/10* (2006.01)
  *A61B 34/00* (2016.01)

(52) U.S. Cl.
  CPC ...... *A61B 1/00078* (2013.01); *A61B 1/00147* (2013.01); *A61B 34/70* (2016.02); *A61B 34/71* (2016.02); *B25J 9/1085* (2013.01); *A61B 2034/715* (2016.02); *Y10T 74/20323* (2015.01)

(56) References Cited

U.S. PATENT DOCUMENTS

| | | | | |
|---|---|---|---|---|
| 4,712,969 A * | 12/1987 | Kimura | ...................... | B25J 9/06 148/402 |
| 4,900,218 A | 2/1990 | Sutherland | | |
| 5,317,952 A * | 6/1994 | Immega | ................... | B25J 9/104 74/490.04 |
| 6,875,170 B2 | 4/2005 | Francois et al. | | |
| 8,568,302 B2 * | 10/2013 | Donhowe | .......... | A61B 1/00009 600/118 |
| 8,578,810 B2 * | 11/2013 | Donhowe | .............. | A61B 17/00 600/141 |
| 8,863,608 B2 * | 10/2014 | Fischer | .................... | B25J 9/142 74/490.04 |
| 9,220,398 B2 * | 12/2015 | Woodley | .............. | A61B 1/0053 |
| 9,221,179 B2 * | 12/2015 | Hinman | .................. | A61B 17/29 |
| 9,393,702 B2 * | 7/2016 | Kim | .......... | B25J 18/06 |
| 9,549,666 B2 * | 1/2017 | Hebert | ................. | A61B 1/0057 |
| 9,549,720 B2 * | 1/2017 | Simaan | .............. | A61B 1/00006 |
| 9,572,628 B2 * | 2/2017 | Zubiate | .................... | B25J 18/06 |
| 2006/0156851 A1* | 7/2006 | Jacobsen | .................. | B25J 18/06 74/490.01 |
| 2009/0099420 A1* | 4/2009 | Woodley | .............. | A61B 1/0053 600/142 |
| 2009/0314119 A1 | 12/2009 | Knoll | | |
| 2010/0030377 A1* | 2/2010 | Unsworth | .................. | B25J 9/06 700/245 |
| 2010/0234988 A1 | 9/2010 | Buckingham et al. | | |
| 2010/0236352 A1* | 9/2010 | Iida | ........................ | B25J 9/1045 74/490.05 |
| 2010/0332030 A1* | 12/2010 | Larkin | .................... | G01L 5/226 700/245 |
| 2013/0312564 A1* | 11/2013 | Kim | ........................ | B25J 18/06 74/490.04 |
| 2014/0260755 A1* | 9/2014 | Dong | ...................... | B25J 18/06 74/490.04 |
| 2016/0016319 A1* | 1/2016 | Remirez | .................. | B25J 18/06 74/490.04 |
| 2016/0311108 A1* | 10/2016 | Alambeigi | ................. | B25J 9/06 |

OTHER PUBLICATIONS

Jamming as an Enabling Technology for Soft Robotics, E. Steltz, et al (iRobot G&I Research; James Franck, Institute, The University of Chicago) Believed to be published Apr. 9, 2010.
Design and Analysis of a Robust, Low-cost-Highly Articulated Manipulator Enabled by Jamming of Granular Media—Nadia Cheng, et al Robotics and Automation (ICRA), 2012 IEEE International Conference, May 14-18, 2012 (See Conference Info as Non-Patent Literature Entry #4 below).
Conference information relative to the Robotics and Automation (ICRA), 2012 IEEE International Conference, May 14-18, 2012) See Non-Patent Literature Entry #3 Above—Design and Analysis of Robust, Low-cost-Highly Articulated Manipulator Enabled by Jamming of Granular Media—Nadia Cheng, et al).
Highly Articulated Robotic Probe for Minimally Invasive Surgery, Amir Degani, et al 2006 IEEE International Conference on Robotics and Automation Published May 2006.
Multi-turn, Tension-stiffening Catheter Navigation System, Yi Chen, et al 2010 IEEE International Conference on Robotics and Automation Published May 3, 2010.
Universal Robotic Gripper Based on the Jamming of Granular Material, Eric Brown, et al PNAS—Nov. 2, 2010—vol. 107—No. 44.
Kinematics and the Implementation of an Elephant's Trunk Manipulator and Other continuum Style Robots Michael W. Hannan, et al Journal of Robotic Systems 20(2), 45-63 (2003).
JSEL: Jamming Skin Enabled Locomotion E. Steltz, et al 2009 IEEE International Conference on Intelligent Robots and Systems.
Vaccum Packed Particles as Flexible Endoscope Guides with Controllable Rigidity Arjo J. Loeve, et al Granular Matter (2010) 12:543-554 DOI 10.1007/s 10035-010-0193-8.
Wearable Haptic Display by the Use of a Particle Mechanical Constraint Takashi Mitsuda, et al 10th Symp. On Haptic Interfaces for Virtual Envir. & Teleoperator Systs. (HAPTICS'02) Published 2002.
Modeling and Implementation of Solder-activated Joints for Single-Actuator, Centimeter-scale Robotoic Mechanisms Maria J. Telleria, et al 2010 IEEE International Conference on Robotics and Automation.
Vacuumatics; Shaping Space by "Freezing" the Geometry of Structures Frank Huijben, et al Tectonics Making Meaning Believed to be Published in 2007.
Vacuumatics; Systematic Flexural Rigidity Analysis =rank Huijben, et al International Association for Shell and Spatial Structures (IASS) Symposium 2010.
Design of a Modular Snake Robot—Wright, et al 2007 IEEE/RSJ International Conference on Intelligent Robots and Systems Published Oct. 29, 2007.
Festo Drives Automation Forwards—Mike Wilson Published 2011.
Design and Analysis of a Soft Mobile Robot Composed of Multiple Thermally Activated Joints Driven by a Single Actuator Nadia Cheng, et al Presented at 2010 IEEE International Conference on Robotics and Automation (ICRA) (See Related Conference Information in Non-Patent Literature Entry #18 below).
Information relative to 2010 IEEE International Conference on Robotics and Automation (ICRA) (See related Article—Design and Analysis of Soft Mobile Robot Compoosed of Multiple Thermally Activated Joints Driven by a Single Actuator listed in Non-Patent Literature Entry #17 above).

* cited by examiner

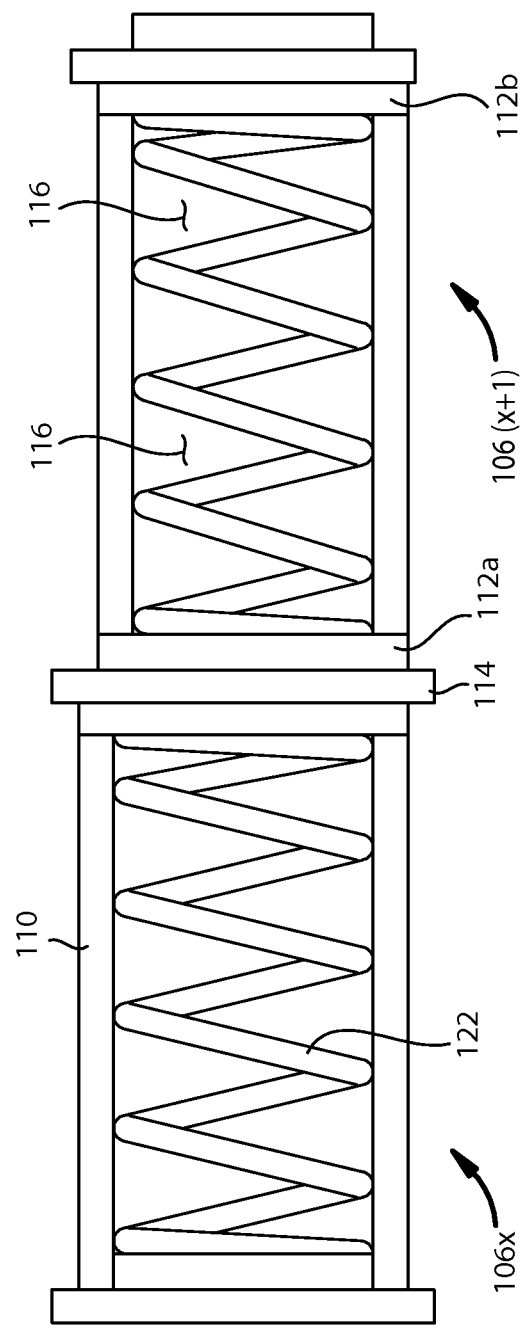

FIG. 4
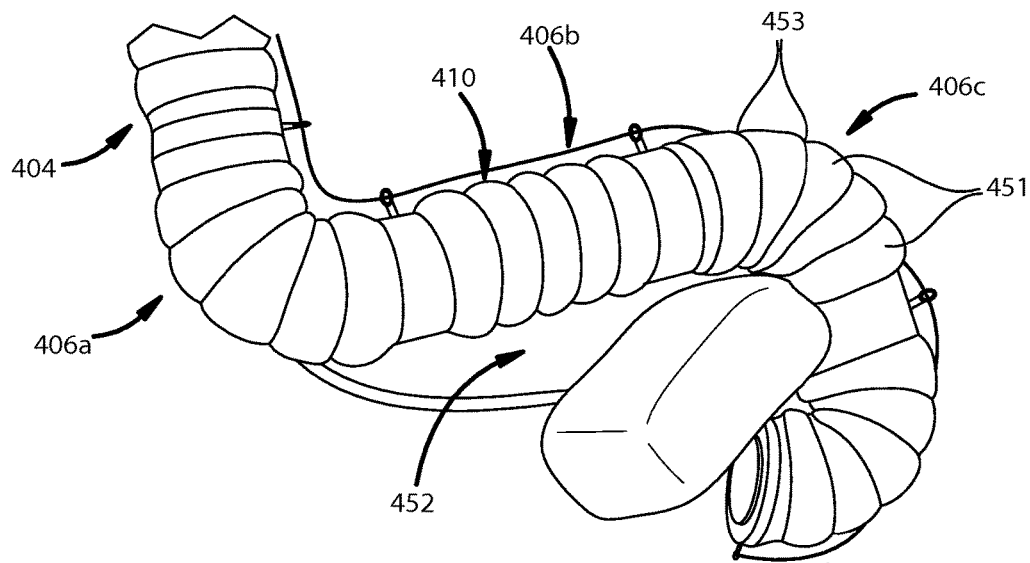
FIG. 5
FIG. 6
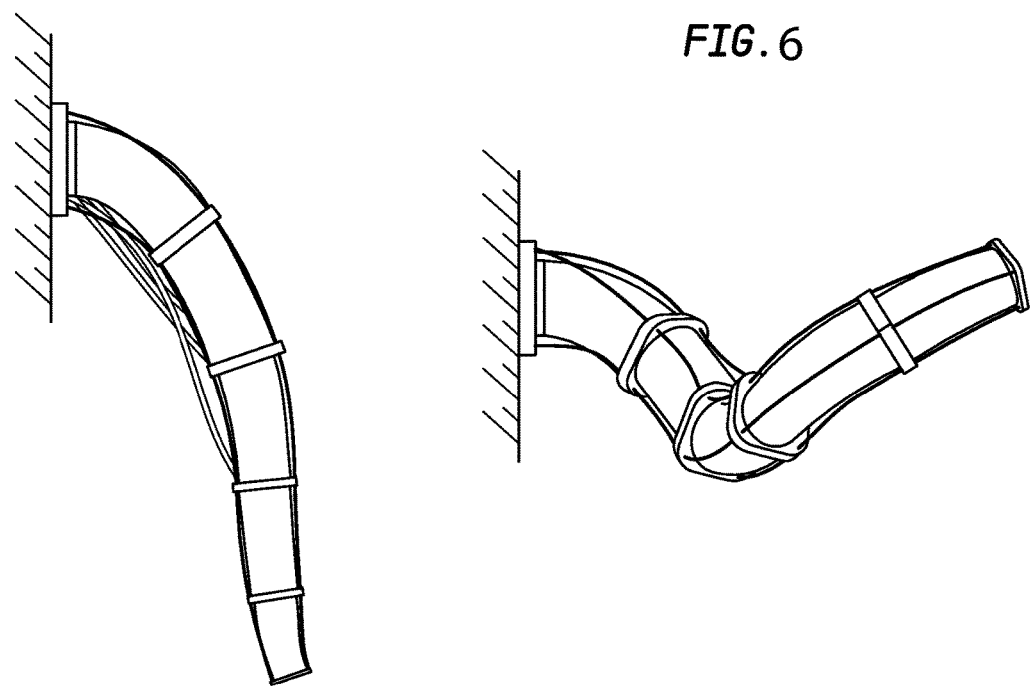

CONTINUUM STYLE MANIPULATOR ACTUATED WITH PHASE CHANGE MEDIA

RELATED DOCUMENTS

This is the 35 U.S.C. §371 U.S. National Phase of Patent Cooperation Treaty application No. PCT/US2013/030354, entitled, CONTINUUM STYLE MANIPULATOR ACTUATED WITH PHASE CHANGE MEDIA, International filing date of 12 Mar. 2013, to which the benefit of priority is hereby claimed. The PCT application claims the benefit of U.S. Provisional application No. 61/646,280 filed on May 12, 2012, entitled CONTINUUM STYLE MANIPULATOR ACTUATED WITH PHASE CHANGE MEDIA AND TENSILE ELEMENTS. The entire disclosure of each application mentioned above is hereby incorporated fully herein, by reference.

GOVERNMENT RIGHTS

This invention was made with government support under Grant No. W911NF-11-C-0201 awarded by the Army Research Office. The government has certain rights in this invention.

INTRODUCTION

Conventional robotic manipulators can be fragile, expensive, and limited in their flexibility, due to the distributed rigid and bulky actuators that are typically used to achieve the precision and degrees of freedom (DOFs) required. Much effort in this area has been in developing snake robots, as they often require many controlled DOFs. While these traditional snake robots have impressive capabilities and are useful in many applications such as search-and-rescue, they can be complex, fragile, and expensive. Often, these types of robots employ one traditional actuator, such as motor, per degree of freedom.

A class of hyper-redundant manipulators that seeks to maximize mechanical compliance is hydrostatic robotics, which often utilize fluidics (hydraulics and pneumatics) for actuation. These types of robots are typically designed to mimic biological systems, as many applications can greatly benefit from robots that have the strength and dexterity of natural structures such as tongues, tentacles, and trunks. Such systems are not typically capable of both passively conforming to their environments and maintaining complex, arbitrary configurations. A subset of such manipulators is sometimes referred to as continuum style manipulators.

Cable-driven systems can be controlled by traditional actuators, such as motors, and are also highly dexterous. These manipulator-type systems are often found in (but not limited to) surgical devices, which typically are too small to include on-board actuators. While many cable-driven robots are capable of being highly articulated, it would sometimes be desirable to lock arbitrarily located segments along the length of the device against relative movement. Many of them lack the ability to lock arbitrary segments in place, thus complicating the control of the robot.

Manipulators that have distributed actuators along their lengths necessarily subject the actuators to the environments in which the manipulators operate. In many cases, these environments are harsh, either in terms of temperature, chemical content (such as in a gas chamber, or within a liquid environment). Thus, it is sometimes a challenge to provide an actuator that can withstand the environment. If it were possible to achieve actuation in the environment without placing an actuator within the environment, that would be beneficial.

Further, manipulators with such distributed actuators must support the weight of the actuators distant from the base support of the manipulator, either through the stiffness of the manipulator itself, or some auxiliary means. The further from the base that an actuator is located, the more moment that its mass applies to the base and the intervening links and joints. Thus, if it were possible to achieve actuation without placing actuators along the length of the manipulator, and thus avoiding this mass and moment load on the base and intervening links, that would be beneficial.

Conventional manipulators composed of rigid links and joints may have pinch-points adjacent their joints, in which delicate items, such as parts of a human or animal counterpart might be pinched. The word counterpart will be used herein to mean a living manipulator operator, or subject, or patient, as the case may be, in instances where it is not important to distinguish among these different agents. For instance, for surgical tools to be used inside or outside a counterpart's biological body, these pinch points might catch the counterpart's flesh tissue, or other delicate parts within them. If it were possible to provide a manipulator with no, or with few pinch points, that would be beneficial.

Conventional manipulators are also typically composed of rigid, hard materials. Thus, in environments where the manipulator operates near or interacts with living humans (or animals), there is a risk of injury to the humans or animals, in the case of inadvertent forceful or high-momentum contact of the robot with the human. For example, manipulators that are used for surgical operations, such as in connection with an endoscopic or proctoscopic examination or procedure, are inserted into a living patient's body. Conventional manipulators are composed of metal, plastic, or other relatively hard, inflexible material. Thus great care must be taken to not injure the human operator or patient, such as through overly forceful pressing, expansion, pulling, etc. of the device within or near to the living counterpart. Further, assembly line robots that swing, extend, turn and grip might injure an operator if contact were to be made. Thus expensive and inconvenient enclosures must be provided around such robots. If it were possible to provide a manipulator that were so safe that such enclosures were not necessary, that would be beneficial.

Manipulators that interact with living counterparts must be safe to operate. Thus, they must be able to assume a safe configuration rapidly, so as not to injure the living counterpart.

It may sometimes be desirable for a manipulator to conform its shape to that of its environment, such as when it must grip and retain an object. To do this with conventional manipulators requires a complicated control scheme.

Conventional robots often have a limited workspace, due to their rigidity. For instance, they may be able to access locations around the surface of a sphere, but are not able to access locations that are radially inward of the outermost spherical surface.

OBJECTS OF INVENTIONS

Thus, objects of inventions hereof include to provide a manipulator that is relatively robust, inexpensive and typically under-determined, i.e., not capable of controlling all possible degrees of freedom, lacking in parts that are rigid or hard, or, if not lacking, then making only minimal use thereof. A further object is to provide a manipulator that is safe around living counterparts. Another object is to provide a manipulator that is able to conform to its environment, including living counterparts, and, if possible to do so passively, without the shape of the environment being specified by model or operator input. It is a further object of an invention hereof to be able to lock arbitrary segments along its extent in desired configurations. It is also an object of inventions hereof to provide a manipulator that subjects none or a minimal number of actuators to any environment in which manipulator effecter operates. All, or most actuators should optimally be located at a base that remains out of the operating environment. It would also be desirable to provide a manipulator that operates within an environment, possibly a harsh environment, without necessitating also providing an actuator in that harsh environment. It would be desirable to achieve manipulator shape conformation with its environment with a control scheme that is simple, robust and reliable. A further object of inventions hereof is to operate within a workspace that is as near to a sphere around a base of a manipulator, as possible, including not only the outer surface of such a sphere, but also radially inward locations, for instance at a location of half the radius of the maximum sphere, or even near to or at the center of the sphere.

These and other objects and goals of inventions hereof will be understood with reference to the Figures of the Drawings, which are:

BRIEF DESCRIPTION OF THE FIGURES OF THE DRAWING

FIG. 2 is a schematic cross-sectional representation of adjacent modules of a manipulator of an invention hereof;

FIG. 4 shows, schematically, a different, uniform diameter embodiment of an apparatus invention hereof, with a bellows-like outer envelope structure;

FIG. 5 shows, schematically, the apparatus of FIG. 3A, in a state where all of the modules are in the not-jammed state;

FIG. 6 shows, schematically, the apparatus of FIG. 3A, in a state where all of the modules are in a jammed state, assuming a relatively horizontal and curved position against a gravitational field;

FIG. 8A coarsely ground coffee; FIG. 8B finely ground coffee, FIG. 8C sawdust; bottom row, left to right: FIG. 8D solid glass spheres; FIG. 8E hollow glass spheres; and FIG. 8F diatomaceous earth;

SUMMARY OF INVENTIONS

A class of manipulator is disclosed herein that is robust, high-force, low-cost, and highly articulated, without employing traditional actuators mounted at the manipulator joints. Rather, local tunable stiffness is coupled with off-board spooler motors and tension cables to achieve complex manipulator configurations. Tunable stiffness is achieved by reversible jamming and unjamming of granular media, which—by applying a vacuum to enclosed grains—causes the grains to transition between solid-like states when jammed and liquid-like ones when not-jammed. Other phase change media may also be used rather than jammable media.

Figure 1:
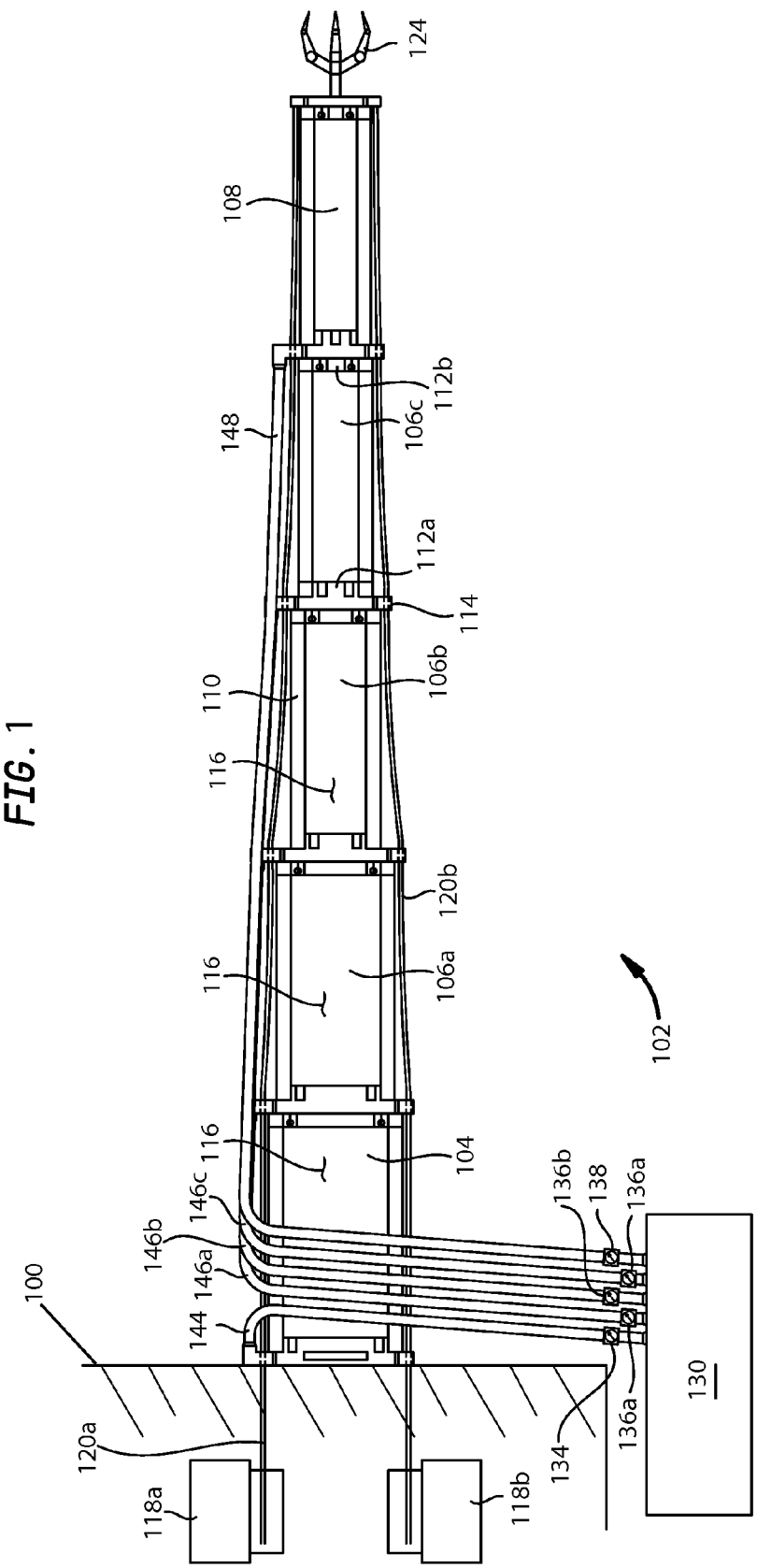
FIG. 1 is a schematic cross-sectional representation of a representative manipulator of an invention hereof.

As shown schematically in FIG. 1, a robotic manipulator 102 can be composed of a plurality of serially arranged modules 104, 106a-106c and 108, arranged in a continuum, which can transition between rigid and compliant states via jamming and unjamming of particulate material within them, and tension cables 120a, 120b running along the length of the manipulator and whose lengths are controlled by spooler motors 118a, 118b. By jamming, it is meant the process by which granular media can reversibly transition between fluid-like and solid-like states. Jamming is used as a variable stiffness mechanism in each module of the manipulator. Because granular systems inherently lack mechanical structure in their not-jammed states, their flexibility and high degrees of freedom can be beneficial for manipulator systems. Serial jammable modules (also referred to herein as segments) can be composed of thin flexible, fluid impermeable membranes 110 containing granular material 116. Jamming can be achieved by applying a vacuum within the modules to create a differential jamming pressure.

A manipulator composed of a continuum of any number of linearly adjacent modules requires only three sets of a motor and a cable to control three DOFs of every module, and therefore, create any arbitrary overall shape for the extended manipulator.

This novel design for a manipulator, and use of jamming for robotic applications in general can greatly benefit many applications, such as human-safe robotics and systems in which robots need to exhibit high flexibility to conform to their environments. The control of the conformation of the manipulator can be robust and elegant. For instance, as shown with reference to FIGS. 4 and 3F, the manipulator can wrap around an object using binary local control (i.e. controlling individual modules to assume one of two states: jammed or not-jammed) and off-board control of the tension cables. The not-jammed modules can passively conform to other objects. The disclosed manipulator is able to fold back on itself, as shown schematically in FIG. 3C and maintain highly articulated configurations via jamming. The reachable workspace boundary of the manipulator is nearly a sphere with a radius equal to the manipulator length.

Method inventions disclosed herein include a method of conforming a manipulator as disclosed herein, to a desired shape. The method entails unjamming all of the modules, and then moving the module that is closest to the ground, or base, to assume the position it has in the desired shape. That positioned module is then jammed. Positioning of the unjammed module can be by actuating the actuator and tensile element, or by hand, or by positioning by another device. Next, the module adjacent to the base, now positioned module is unjammed, and is moved to the position it has in the desired shape. That positioned module is then jammed. This procedure is carried out serially along the length of the manipulator until its entire extent is positioned as desired. It is not necessary that all of the as yet unpositioned modules be in either a jammed or not jammed state, while the module in question is being positioned. What is important is that the module being positioned be in the not-jammed state as it is being positioned, and then be jammed afterwards, and stay jammed.

The manipulation of claim 1 at least two of said modules having different cross-sectional areas from each other.

A more extensive summary is provided near the end of this disclosure, preceding the Aspects and Claims.

DETAILED DESCRIPTION

FIG. 1 illustrates schematically in cross-section, a representative implementation of a jammable manipulator 102. The manipulator is coupled to ground 100 (shown as a wall) through a base module 104. Intermediate modules 106a, 106b and 106c couple the base module 104 to a terminal module 108. As shown more clearly in FIG. 2, each module is composed, in part, of an envelope 110, which is coupled to a basal end cap 112a and a terminal end cap 112b, arranged toward the base module 104 and the terminal module 108, respectively. Each envelope is fluidically isolatable from the ambient environment, so that a relatively lower pressure, such as a vacuum, or close to a vacuum, when air is the fluid, as compared to atmospheric pressure, can be maintained within each module. The fluid can be air, water, or any other suitable working fluid. Typically, it is air, and the examples shown herein use air as the working fluid.

It is also possible, as explained below, to establish a pressure within each envelope that is greater than atmospheric pressure, for instance to un-jam the particles, or even to establish some rigidity in the envelope walls, such as with an inflated balloon. It should also be noted that the pressure within each module can be independent of the pressure within any other module. The pressure within different modules can be different. If so, it may be most convenient to provide a different pressure source for each module, or, some sort of regulating valve between the pressure source and the module. Or, multiple valves can be used for each module. The end caps mechanically support each envelope, and also may include mating configurations, so that adjacent modules may be secured to each other. Alternatively, a separate joint element 114 may be provided between end caps 112a and 112b of adjacent modules, for instance, 106a and 106b. The apparatus is modular. Modules can be added to make the device longer, and they can attach to each other via any suitable coupling means. The number of tension elements does not need to increase as modules are added. And, using a spooler motor, which pays out and reels in tension element length, all that need be done to add or delete a module is to wind or unwind more or less tensile element upon the spooler motor. The tensile elements do need to be coupled to each module, such as at the end caps. A fluid conduit also would need to be added for each module.

Each envelope contains a volume of a particulate media 116 that can exist in either a jammed, solid-like state or a not-jammed, liquid-like state, as described below in more detail. For instance, ground coffee has been found to provide excellent results for a class of prototypical configurations. The reasons for this are also discussed below in detail. In general, phenomena other than jamming can also be used to actuate the modules of the manipulator, and these phenomena are referred to generally below as phase-change phenomena. Jamming is an instance of the type of phase-change of interest, and will be used initially to illustrate general principals of inventions hereof. However, it will be understood that these jamming embodiments are meant to be illustrative only, and not limiting. Thus, rather than a jammable material being contained in each envelope, more generally, a phase-change material can be contained in each envelope.

Two actuators, 118a and 118b are shown. Each actuates a tensile element 120a and 120b, respectively. The actuators may be spooler motors, or any suitable actuator that can reel in and release additional length of tensile element. Spooler actuators will be used to mean any such device. The tensile elements may be cables, such as metal or synthetic (e.g., polymer, fiber, or a combination thereof) cables. An important aspect of manipulators of inventions hereof is that a manipulator 102 composed of any number n of modules 106x, requires only three sets of an actuator, such as A18a, and a tensile element such as 120a, to control: three DOFs of each of the modules 104, 106a-106n and 108; three DOFs of the tip of the manipulator; and 3×n DOFs for the entire manipulator. By a set it is meant one actuator and one tensile element.

Figure 9:
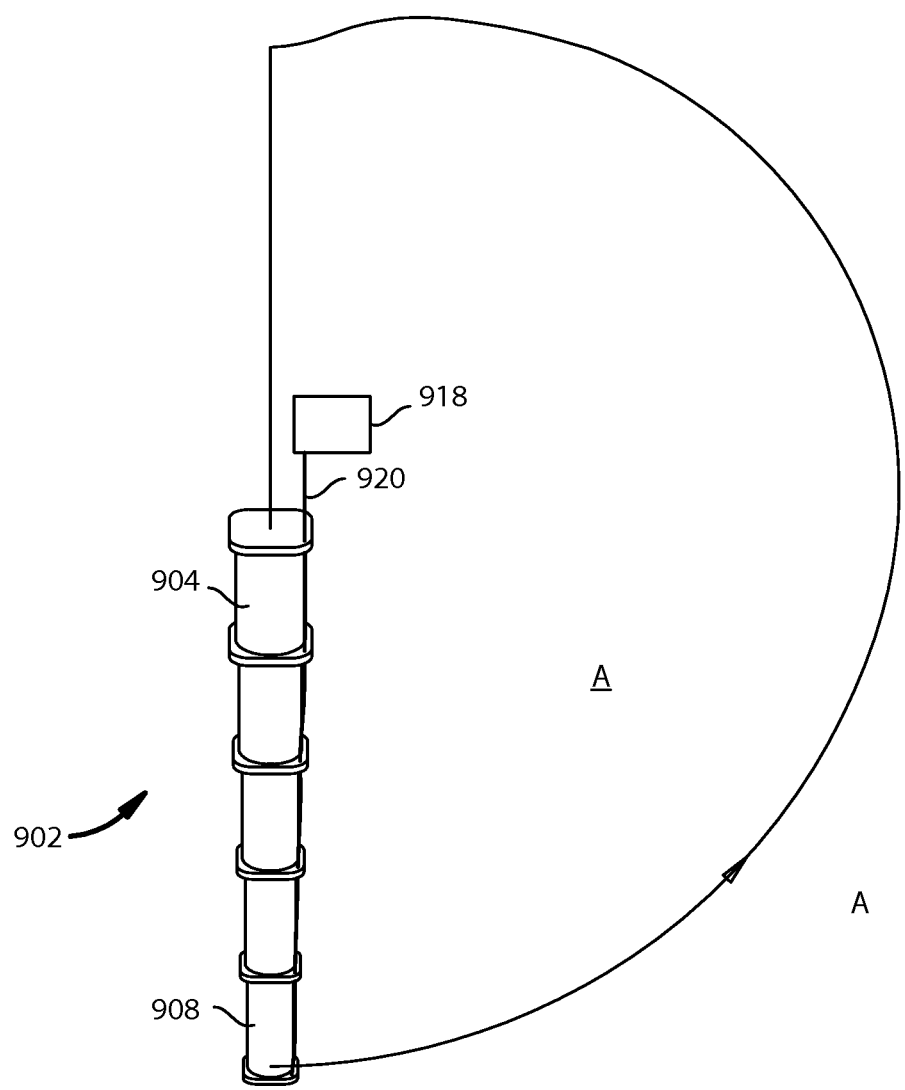
FIG. 9 shows, schematically, a work space that can be achieved using a manipulator having a single actuator and a single tensile element.
Figure 10:
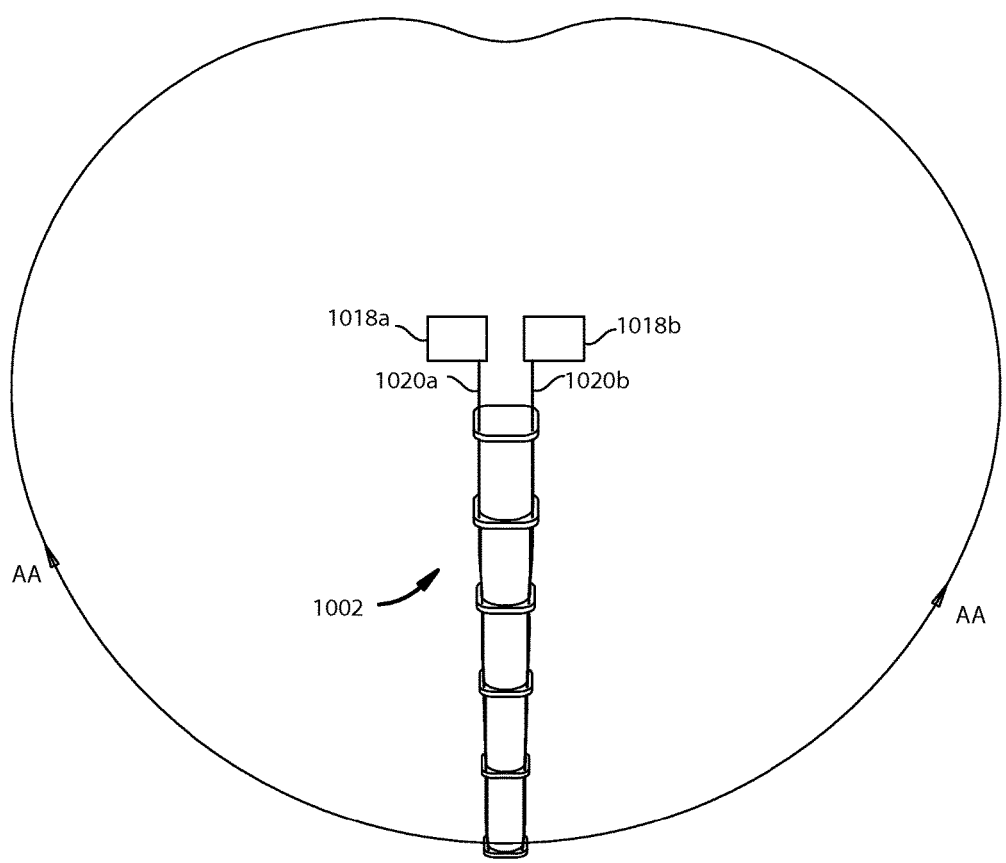
FIG. 10 shows, schematically, a work space that can be achieved using a manipulator having two actuators and two associated tensile elements spaced evenly apart (directly across from each other)
Figure 11:
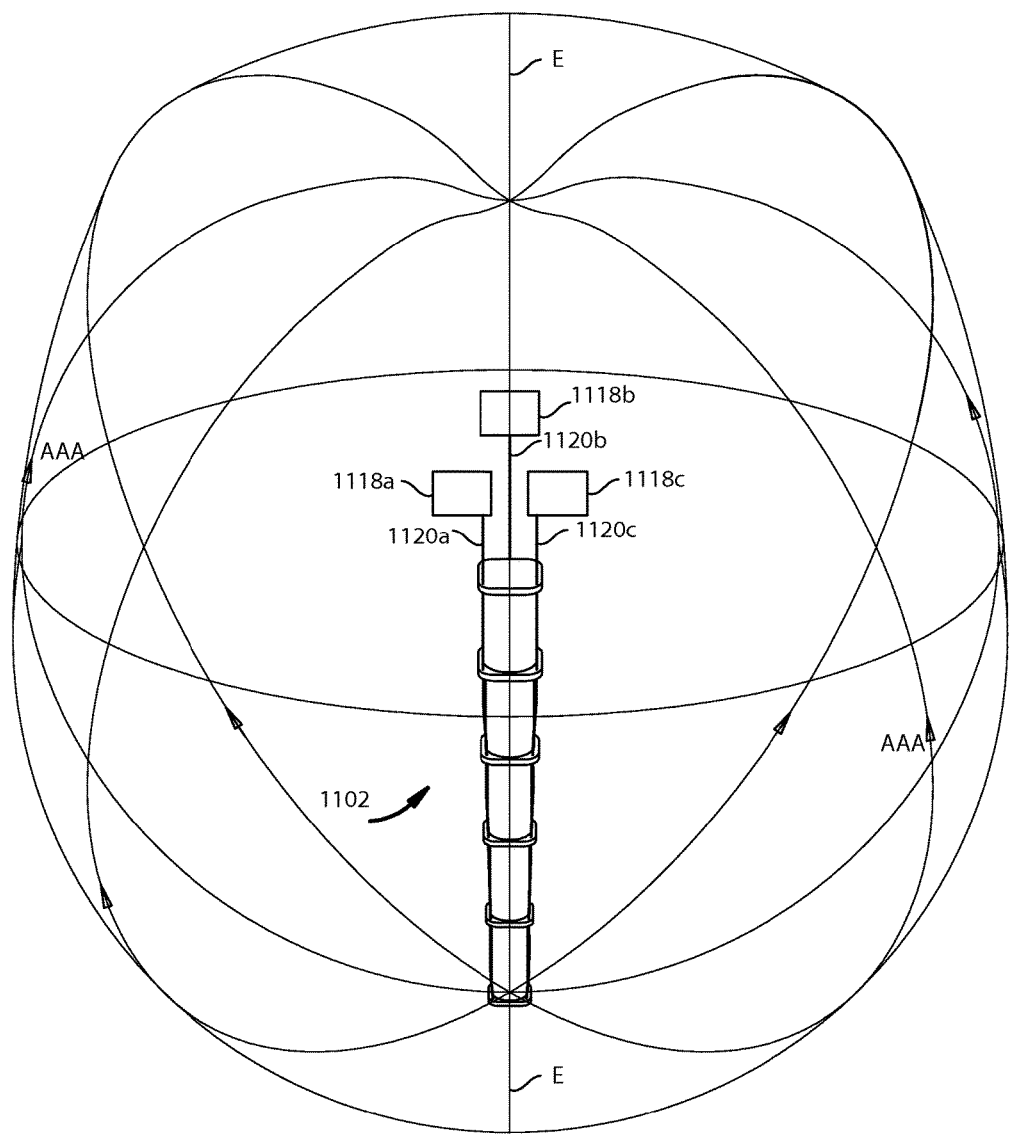
FIG. 11 shows, schematically, a work space that can be achieved using a manipulator having three or more actuators and associated tensile elements, spaced evenly apart.

With reference to FIGS. 9, 10 and 11, operation of the actuators and the tensile elements are shown. FIG. 9 shows a manipulator 902 that is actuated by a single actuator 918 and a single tensile element 920. By applying tension to the tensile element 920, the manipulator 902 can sweep through the arc A of approximately 180 degrees in a single plane, which plane includes the tensile element 920. The degree to which the distal module can be driven close to 180 degrees depends on the flexibility and length of the plurality of modules, and on a combination of the friction angle (which is related to resistance to motion of the particles) and the flexibility of the membrane, and possible locations for the actuator. The manipulator can be held at any position to which it can be drawn by the actuator and tensile elements, by jamming the modules at a time when the modules are in a configuration desired to be held. It should be noted that the tip of the manipulator 902, with its terminal module 908 can be brought to any location within the area A bounded by the curve A and the manipulator 902. The area A is reminiscent of one half of a cross-section of an apple, a circle that is slightly squashed at one end of the diameter defined by the extent of the manipulator. It is important to point out that for the tip 908 of the manipulator to be able to reach the full extent of positioning furthest away from its rest position, at least the base module must be bent back nearly fully on itself.

The concept of friction angle is used to determine the strength of granular systems such as soil and other similar media, such as jammable media. As used herein, the friction angle, also known as the angle of internal friction, is the angle on a graph (Mohr's Circle) for a given particulate media, of the shear stress and normal effective stresses, at which shear failure occurs. In general a granular medium with relatively larger friction angle exhibits, a relatively larger shear strength. What is desired for the present context is a relatively large friction angle when in a jammed state, and a relatively low friction angle when in a not-jammed state.

FIG. 10 shows a manipulator 1002 that is actuated by a pair of actuators 1018a and 1018b and a pair tensile elements 1020a and 1020b, spaced evenly about the radial cross-section of the manipulator. By applying tension to the tensile elements 1020a and 1020b, the manipulator 1002 can be brought to any location within the area AA of approximately 360 degrees, in a single plane, which plane includes the tensile elements 1020a and 1020b. The workspace is again sort of squashed circle with a radial extent on one direction equal to the manipulator length, and slightly less on the opposite, squashed direction. Typically, when tension is applied to one tensile element, e.g., 1020a, it is not applied to the other, e.g. 1020b. However, simultaneous tension can be applied to aid in stability and control, or to actuate in the axial or compressive direction (the third DOF).

FIG. 11 shows a manipulator 1102 that is actuated by at least three actuators 1118a, 1118b and 1118c and three tensile elements 1120a, 1120b and 1120c. The actuators are spaced equally apart, 120 degrees from each other around the axis E of elongation of the actuator. By applying varying degrees of tension to the tensile elements 1120a, 1120b and 1120c, typically simultaneously, the terminal module of the manipulator 1102 can be brought to any position within the volume AAA of approximately nearly a sphere, which is centered near to the base module 1104. The patterns of how much tension to apply to each tensile element to achieve a desired location for the distal element 1108 or overall shape for the entire manipulator can be determined by one of skill in the art based on the image provided. As with the one and two actuator embodiments, the distal module 1108 can be swept through nearly the entire volume AAA, which is a sort of squashed sphere with a radial extent on one hemisphere equal to the manipulator length, and slightly less on the squashed side.

It is also reasonable to use one or two actuators and tensile element sets more than are minimally required from geometric and mathematical requirements, to achieve a more complete coverage of a workspace with less complicated cable tensioning and module jamming control routines. For instance, rather than using three such sets to achieve the work space shown in FIG. 11, four such sets could be used, spaced equally around the manipulator at 90 degrees apart.

Thus, the disclosed manipulator is able to fold on itself and maintain highly articulated configurations via jamming. The reachable workspace boundary of the manipulator using three or more tensile elements is nearly a sphere with a radius equal to the manipulator length, as shown in FIG. 11.

A significant aspect of inventions disclosed herein is that the shape of the manipulator can be established by changing the shape of a module when it is in a not-jammed state, and then jamming that module, which solidifies the module, thereby allowing it to retain the shape in which it has been put. When not jammed, each module can be shaped and arranged relative to adjacent modules as desired, principally by adjustment of the tension elements, but also by other means. Then, the module or modules are jammed, thus solidifying the overall manipulator in the desired shape.

Before discussing changing and controlling the shape of the manipulator by jamming, a brief discussion of jamming in general is instructive. By jamming, it is meant the process by which granular media can reversibly transition between a fluid-like and a solid-like state. Jamming is used as the variable stiffness mechanism in each module of the manipulator. Because granular systems inherently lack mechanical structure in their not-jammed states, their flexibility and high degrees of freedom can be beneficial for manipulator systems. Serial jammable modules can be composed of thin flexible membranes that are impermeable to the working fluid, containing granular material. Jamming can be achieved, in the case of gas, such as air, by applying a vacuum within the modules to create a differential jamming pressure.

As shown schematically with reference to FIG. 1, a pressure differential can be provided by coupling a pump 130 that establishes a pressure that is lower than the ambient, within each module, 106a, 106b, . . . 106n (where n is the number of modules minus two) and also the base module 104 and the terminal module 108. In the case of working with air as the working fluid, the lower pressure can be at or near a vacuum. It need not be a very perfect vacuum, as pressure differentials as small as 0.5 atmospheres have been used.

The pump is selectively and individually coupled to each module through a set of corresponding valves 134, 136a, 136b, . . . 136n and 138, for instance solenoid valves. The valves can be located all together, as shown in FIG. 1, away from the manipulator, with an individual conduit 144, 146n, 148, etc. running from each valve to each module. Or, a single line can run along the length of the manipulator, and a valve can be located at a branch conduit to reach respective module. The pneumatic conduits may be external to the module envelopes, or internal, for instance within a central lumen. This can be so whether there the valves are located off-board of the manipulator, such as shown in FIG. 1, or upon or within the manipulator, adjacent each module.

In general, when in a not-jammed state, the manipulator is conformed to a desired shape, by one of several techniques, discussed below. All or selective ones of the modules are placed in a jammed state, and the overall manipulator becomes substantially rigid in the desired shape.

This individually addressable jamming capability allows the manipulator to effectively achieve Z×Y DOFs, where Z is the number of modules and Y is the number of DOFs per module. Position control was performed by selectively jamming/unjamming individual modules and controlling the length of the tension cables.

Jamming is a useful variable stiffness mechanism for robotic applications due to its simplicity and combination of a relatively fast activation time (on the order of milliseconds) and the capability of transitioning between compliant states and rigid, load-bearing ones.

Jamming according to a definition used in physics, is defined when a collection of grains has a yield stress. Ordinary liquids do not have a yield stress, as they flow under any external force. However, solids require a certain amount of stress to deform; this required amount of stress is called the yield stress. Grains do not necessarily have to be fully jammed or not-jammed; one can imagine grains slipping and catching so that they transition between jammed conditions and not-jammed ones. Enclosed grains under vacuum can have varying degrees of rigidity due to different applied vacuum pressures. These may be considered intermediate states of rigidity.

It is also helpful to consider that the effective phase transition that occurs in jammed systems is analogous to what is observed in microscopic systems with attractive particle interactions. Jamming, or when the effective solid phase is achieved, can occur only when the density of particles exceeds a threshold. As seen in many materials at the microscopic scale, systems can become not-jammed, or achieve the effective liquid phase, when the temperature is raised (e.g., when the system is under vibration) to a critical value or when the material is sheared enough to cause the particles to move relative to each other. While significant work has been done in the physics community to understand how different grain parameters, such as shape and size distribution affect the jamming transition, researchers have only recently begun to study jamming for robotic applications. To transition between loose, flowing grains and rigid, interlocked ones presents an interesting problem. Because inter-particle friction is primarily based on constant, physical grain parameters, grains that exhibit relatively low inter-particle friction should flow well in the not-jammed state and should also form a weaker solid in the jammed state, than particles with higher inter-particle friction, and vice versa. Grain properties and their effects on jamming are discussed below.

Typically, the granular material is grains 116 (FIG. 1) loosely packed into the thin envelopes 110. It is not critical how the granular material is packed in the envelope. It is useful to place in as much as possible without expanding the envelope. However, this is not necessary. The amount of material within affects the maximum strength of the jammed structure, so that it can be user-determined.

Returning to a discussion of a typical manipulator, as shown in FIG. 2, which is an enlargement of two representative adjacent modules 106x and 106x+1, each module 106x includes a low stiffness compression spring 122 along its length to help constrain the bending motion of each module. This improves its precision while still being soft enough to maintain the overall flexibility of the manipulator. The springs 122 also serve as force-restoring elements to help return modules to a neutral position when not-jammed. By neutral position, it is meant with the modules' axes of elongation E aligned. Employing springs 122 with outer diameters equal to those of the envelopes 110 of the modules in which they are contained additionally maintains the cross sectional area of each segment during bending. This is important to maximize the manipulator's ability to support payloads in the jammed state, as granular material tends to squeeze out of the mid-length portion of the modules upon bending. This latter purpose can be achieved alternatively by building structure into the envelope 110, for instance, such as shown at FIG. 4, by using a bellows-like shape, having constricted creases 453 between bulging outward sections 451, to prevent envelopes 410 from buckling during bending and to help maintain uniform distribution of the grains. Rather than a spiral type spring, a springy foam annulus could also be used.

As shown schematically in FIG. 1, an effector 124 can be provided upon the terminal module 108, in a conventional manner. Any sort of an effector can be used. However, an effector may not be necessary, because as shown in FIG. 4 and FIG. 3F, the overall manipulator extension 452, 352, respectively itself can coil and grasp, much like an elephant's trunk. As shown schematically with reference to FIGS. 3A-3F, and in particular FIG. 3F, showing the manipulator modules, coiled into an approximate circle, and grasping a drinking cup 355.

A notable advantage that a jammable manipulator of an apparatus invention hereof has over traditional systems with rigid links is its flexibility and ability to conform to its environment with simple control. The manipulator can easily wrap around an obstacle using binary local control (i.e. controlling individual modules to assume one of two states: jammed and not-jammed) and off-board control of the tension cables. The not-jammed modules can passively conform to other objects. By passively conform, it is meant that they can be laid across or upon another object, and, by force of gravity, or other external load, conform somewhat to the other object. Or, when the other shape is not gravitationally below the not-jammed manipulator, another agent, such as a human operator, or another robot, can grasp the not-jammed manipulator, move it so that it conforms to the shape of the object, or wrap it around the object, and then the manipulator modules passively assumes the shape of the other object. It can then be actuated, such as by jamming certain of the modules, so that the passively modeled overall shape of all of the modules then becomes actively held. This contrasts with the limited capabilities of the aforementioned existing approaches.

Another matter relates to how to achieve a desired shape. Two different questions arise. One is how to deliver the terminal module 108 or, if present, an end effector 124 to a point in space, without regard to the conformation of the other modules of the manipulator. The second is how to achieve a specific geometrical shape of the full extent of the manipulator in space, such as any of the specific sinuous shapes shown in FIGS. 3A-3F.

Turning first to the task of delivering the end module to a specific location in the work space, there are likely many non-unique solutions to the question of how to conform the extent of manipulator modules to do this. Some will be identical to others, but mirror images around the circumference of the axis of elongation E. Others may be more dissimilar. In any case, for all such solutions, the geometry of the extent of the manipulator can be determined by known geometrical means. This will provide a location for each module along the length of the manipulator, resulting in a conformation, or shape, of the extended manipulator. At that point, this task is the same as the task of how to achieve a specific geometrical shape of the full extent of the manipulator in space, such as any of the specific shapes shown in FIGS. 3A-3F.

There are more than one ways to achieve this. One way is to allow all of the modules to relax, to be not-jammed, and to use the cables to pull the terminal end of the base module 104 to the desired position to assume the root portion of the conformation. The terminal module 104 is then jammed, but the remaining modules are left not-jammed, and the cables and actuators are used to pull the manipulator so that the second module 106a is in the desired position, and then, it is also jammed, so that both the base module 104 and the adjacent module 106a are jammed. The procedure is followed along the extent of the manipulator to the terminal module 108, and by this method the overall conformation of the manipulator is achieved. There may be times when the cables are not able to achieve the desired shape, but the manipulator can be forced by an external force, such as a human operator, or another robotic manipulator.

There are other ways to achieve this, instead of positioning only one not-jammed module at a time. The other ways may require more or faster computational functions. For instance, it is not necessary that all un-positioned modules need be in a not-jammed state. In fact, all but one may be in a jammed state. Typically, the module to be positioned would be the closest one to the most recently positioned module, but this need not be. In any case, the module being positioned must be not jammed.

Yet another related matter is how to move the manipulator from one position in space to another, simply focussing on the effector 124 or end module 108, or focussing on the conformation of the entire manipulator and its position in space, from one such conformation and position to another. Such tasks can be dealt with according to known techniques of motion and position scheduling, such as have been used with existing manipulators, in particular, so called snake robots. A representative method is described in Kinematics and the Implementation of an Elephant's Trunk Manipulator and Other Continuum Style Robots, M. Hannan and I. Walker, Journal of Robotic Systems 20(2), 45-63 (2003), which is fully incorporated herein by reference k. Other general techniques of inverse kinematics and motion planning can be used.

Figure 12:
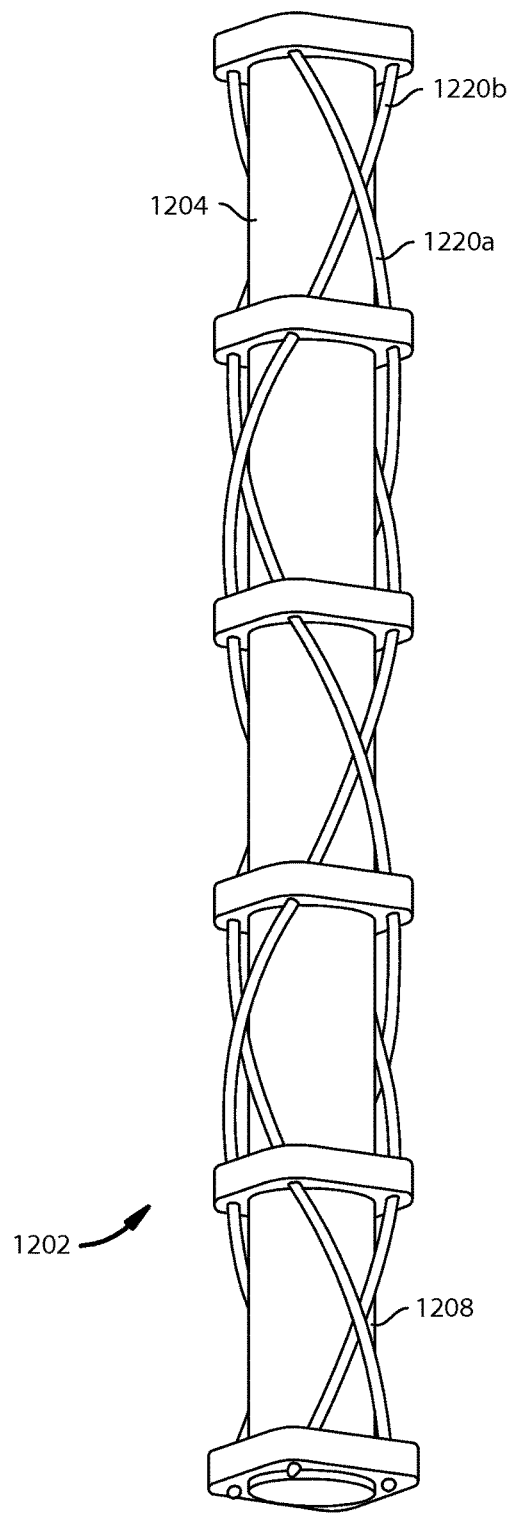
FIG. 12 shows, schematically, a manipulator have four cables that twist around the circumference of the manipulator modules, two spiraling in each chirality, one having a left hand twist, the other having a right hand twist.

Another interesting concept is illustrated with FIG. 12. Cables 1220a and 1220b are provided wrapped around the modules of the manipulator 1202. The two cables 1220a and 1220b twist with opposite chirality around the manipulator, each anchored at opposite ends of a diameter through the base module 1204. Two additional cables are not labelled. However, they would are anchored also at the base module, spaced apart 90 degrees from each of 1220a and 1220b. They wrap around the manipulator similarly, one of each chirality. Each cable is patterned like a screw thread. This allows for controlled twisting motion of the entire manipulator 1202. With four twisting cables there can be four DOF per module.

While jammed granular systems can provide significant compressive strength, their tensile strength is typically limited by (and equal to) the applied differential pressure, assuming that the grains do not mechanically interlock to resist tensile loads. An important capability of cable-driven designs, such as are disclosed herein, is that the cables 120a, 120b, provide significant tensile strength of the manipulator. Experiments have been conducted to determine the strength of a jammed, cantilevered manipulator with and without activating the tension cables 120a, 120b. By loading the terminal module 108 of the manipulator, it was determined that a fully jammed manipulator, with a differential jamming pressure of one atm, yielded at applied loads equal to 30% of its own weight without the use of tension cables and at 200%, with the use of the tension cables (without off-board electromechanical components). In contrast, many industrial manipulators can only support payloads that are a fraction of their own weight. Thus, for many applications, the strength of the tensile elements, particularly as compared to their weight, will be important considerations, with stronger and relatively lighter tensile elements being preferred.

In general, it is important to optimize the strength to weight ratio of all components of these systems, including the tensile elements, jammable or phase change material, etc.

The disclosed systems find applicability for many uses. With increasing need and capabilities for robots to work alongside humans, the disclosed system could greatly benefit human-safe robots, because a jammable manipulator can be very responsive and accommodating to its environment. The manipulator's relatively high degree of flexibility and lack of any permanently rigid components, as compared to conventional link and distributed actuator manipulators, allows the disclosed devices to better conform to their surroundings, for example, to gently wrap around a human counterpart to achieve a desired end effector position. In addition, a granular manipulator's short jamming/unjamming cycle-time can be on the order of milliseconds. Such speed enables a granular manipulator robot to quickly respond to its human counterparts. For instance, if modules of the manipulator need to be softer when in direct contact with a person, they can be made essentially immediately soft.

For instance, when being used in an invasive medical procedure, if the patient moves or the device slips, it can be made, essentially, instantly, harmlessly soft. Further, such a granular manipulator can be equipped with an effector, which is not granular, not soft, for instance, a sharp scalpel. Upon SENSING a dangerous configuration, or event, such as the proximity of a blood vessel, the granular manipulator can be made not-jammed, relaxed, unable to transmit significant force to the scalpel, thereby minimizing its threat to the patient. (As an example from another field, but which can give a sense of what may be done, there are table-saws that sense proximity of a human finger at the spinning blade by some capacitance method, and the spinning blade stops in so short a time that it does not cut the operator. This might be used in conjunction with such a sensor, and rather than stopping the spinning of a blade, the safety action would be that the jammed modules, or some of them, become not-jammed.

Additionally, a conventional robot with links and joints typically has points along its extent that could pinch its environment, including a living counterpart. Such pinch points would need to be avoided. If actuators of such a conventional robot are also located on-board, at the joints, this provides additional pinching hazards. A jammable manipulator, as disclosed, has few, if any pinch points. The external tensile elements are very thin and can be held close to the body of the manipulator. It is also possible, and desirable for many applications, to sheath the entire manipulator, even the tensile elements, in a further flexible envelope, thereby covering up all of the tensile elements.

In general, a system that uses jamming could drastically decrease the cost of robots compared to more traditional approaches. This would allow robots and manipulators to be more affordable and more broadly utilized.

An important aspect of jammable robotic systems is that they can be very low-cost compared to existing devices, due to the small number of electromechanical components (traditional actuators) required. For the four-actuator prototype shown in FIG. 3A the total cost of the manipulator structure and granular material (not including the off-board electromechanical components) was USD$ 80 (the majority of the cost was for the five springs, which cost USD$ 10 each).

A jammable manipulator can be very dexterous and articulated, potentially increasing the capabilities of traditional manipulators in applications such as search-and-rescue. Further, because the cost of the elements is so low, jammable manipulators can be expendable, throw-away components of a rescue operation, which can be discarded in a hostile or distant environment without much expense.

Two or more manipulators, such as shown in FIG. 1, can be used together in concert, akin to fingers of a hand, or pincers. In such a case, the two or more manipulators can share use of the same vacuum pump and other items, such as the control electronics. Or, two or more individual manipulators can be used in an assembly line separately, in a manner similar to the trunks of two or more elephants carrying a log, or handing an item from one elephant to another.

The strength of disclosed systems that operate at an ambient pressure and use vacuum pressure to achieve jamming is limited by the maximum pressure differential that can be achieve below atmospheric pressure, which is fixed. Thus, operation in an environment of higher pressure can make use of the higher pressure differential to achieve greater strength. An area that can exploit this fact is underwater robotics, where the operating environments can generate extremely high jamming pressures and therefore very strong structures. There is nothing inherent in the use of jammable systems that would not work under water, as long as water sensitive components, are protected in conventional manners.

Figure 8:
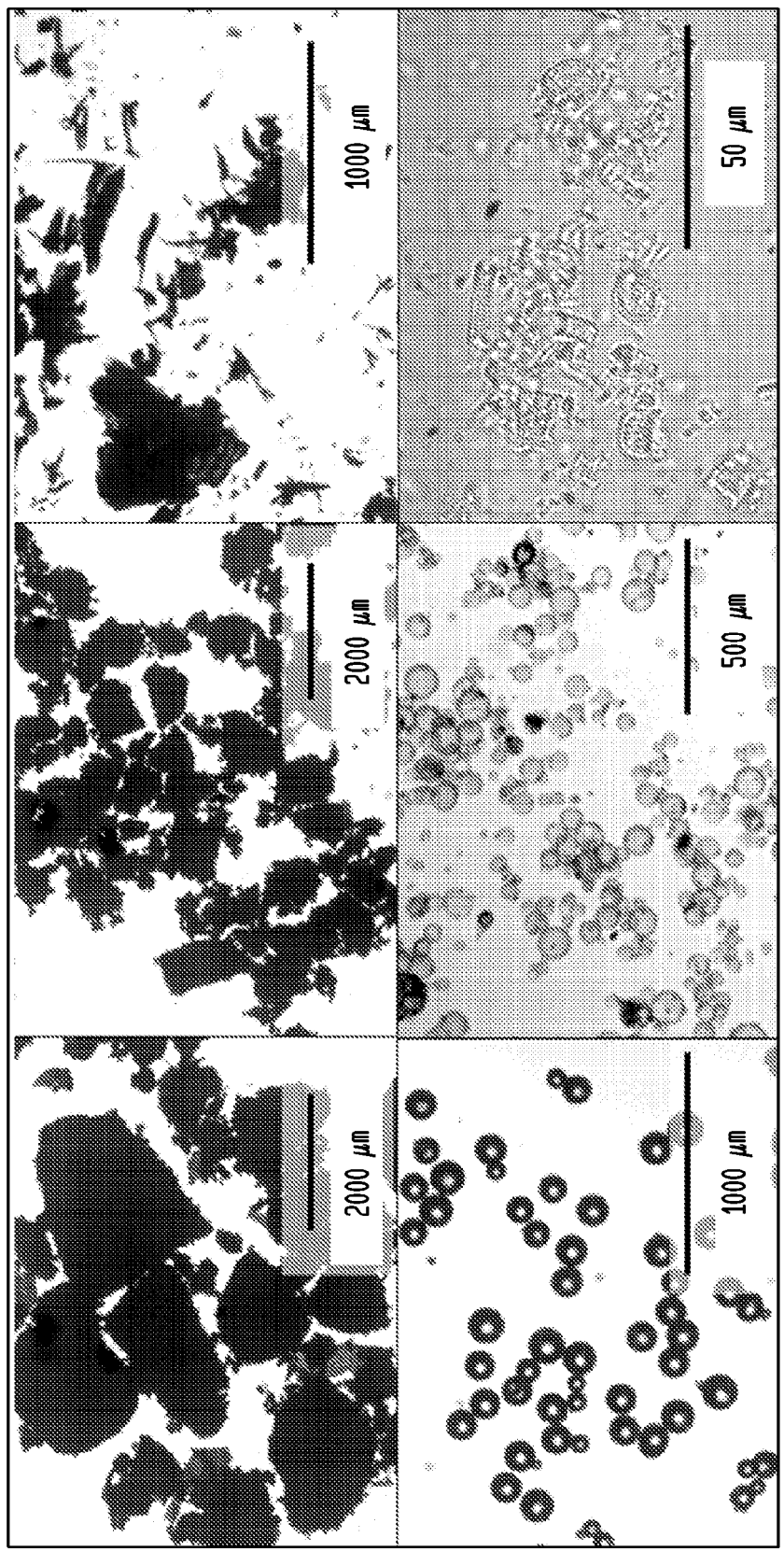
FIGS. 8A-8F show a digital image micrographic representation, of the six different materials for which graphs are shown in FIG. 7, showing, from upper left to right.

The present inventors have conducted studies to evaluate the properties of various granular materials as they relate to manipulators as disclosed herein. Compression tests were conducted on several lightweight granular materials that were hypothesized to exhibit high strength in the jammed state but still able to flow easily in the not-jammed state. Grain characteristics of interest included: high porosity, large size distribution, and large shape distribution. The latter two are known to increase the density and interlocking ability of grains, thus increasing the overall strength of the jammed system. Digital representations of microscopic images of the materials tested are shown in FIGS. 8A-8F, where: FIG. 8A shows coarsely ground coffee; FIG. 8B shows finely ground coffee; FIG. 8C shows sawdust, FIG. 8D shows diatomaceous earth; and FIG. 8E shows hollow glass spheres (10-50 microns diameter). Solid glass spheres (100-200 microns diameter) were also included as a comparison and are shown in FIG. 8F, because they are frequently used as a benchmark shape for granular studies.

Cylindrical test samples, with a diameter and height of 50 mm and 100 mm, respectively, were constructed by loosely packing grains into a thin (approximately 100 microns thick) latex membrane. Loose packing was achieved by dispensing the grains through a funnel and moving the funnel in a circular motion to achieve uniform piling. During this process, sample dimensions were controlled by applying vacuum pressure between the latex membrane and an outer rigid tube to maintain the cylindrical shape. Upon applying a vacuum to the inside of the membrane to jam the grains, the sawdust and diatomaceous earth samples tended to compact significantly, so exceptions were made for these materials in terms of initial packing density to ensure uniform sample dimensions. For all the compression tests, the differential jamming pressure was 75 kPa.

Figure 7:
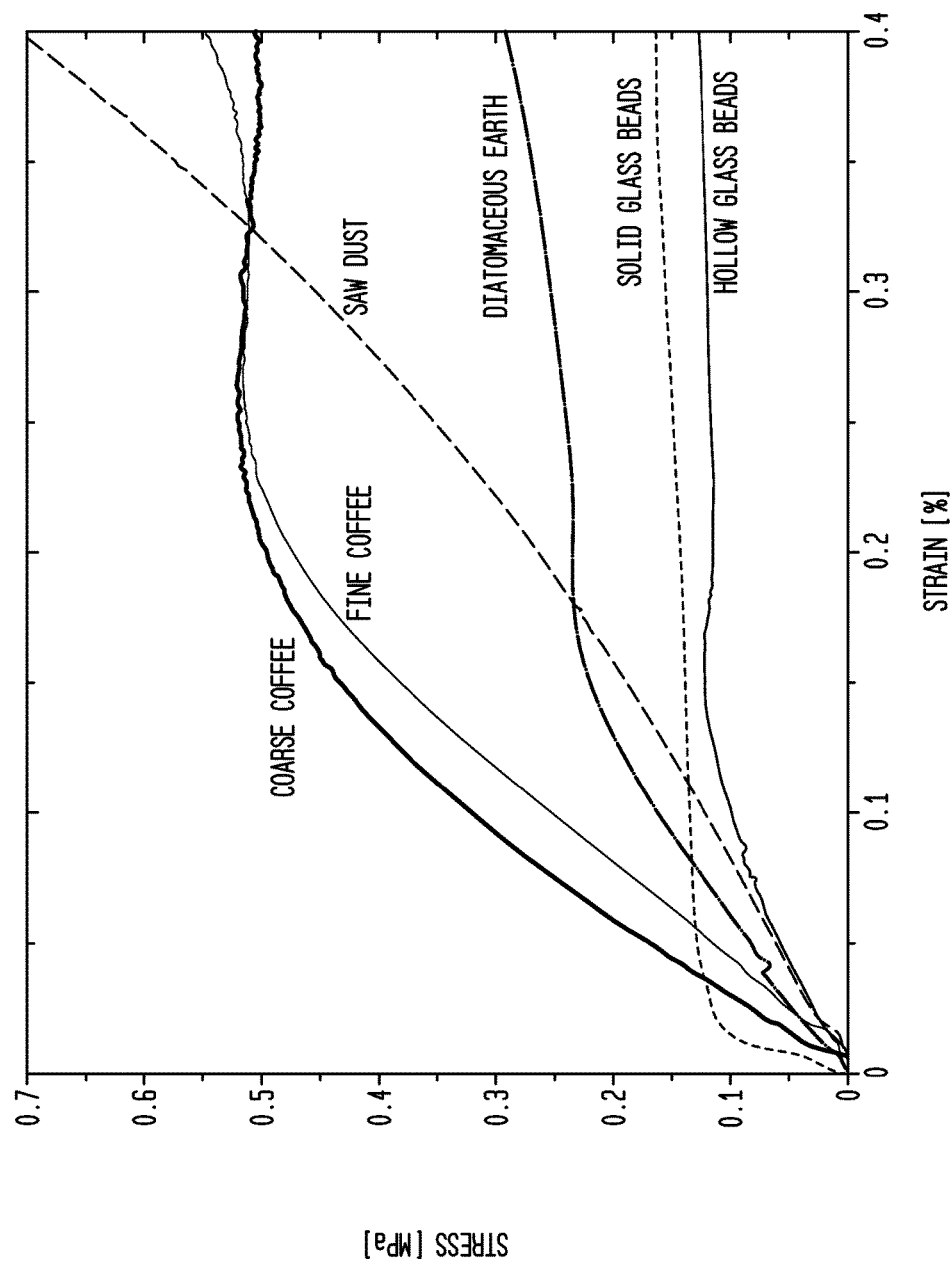
FIG. 7 shows, graphically, the relation between stress and strain for six different particulate materials.

FIG. 7 presents representative stress vs. strain curves, and TABLE 1 includes density and effective compression modulus data for each of the materials tested.

TABLE 1

Density and Effective Compression Modules of Grains

| Grain material | JAMMED DENSITY [KG/M$^3$] | Effective compression modulus/Density [kN-m/kg] |
| --- | --- | --- |
| Hollow glass beads | 83 | 12.8 |
| Coarse coffee | 445 | 6.8 |
| Solid glass beads | 1445 | 5.9 |
| Fine coffee | 505 | 5.4 |
| Sawdust | 400 | 4.2 |

Note that the density values are for the bulk samples before each test with an applied 75 kPa differential jamming pressure. Analysis of the stress-strain curves provides valuable insight about the materials that is not necessarily captured in individual parameters, such as a material's compression modulus or yield stress. For example, while the solid glass beads have the largest effective modulus, their yield stress is barely one fourth of that of the coarsely ground coffee, which had a relatively large effective modulus, making the latter a potentially better option for many applications.

The concave upward shape of the stress-strain curve for sawdust is typical of that of certain materials, such as also a flexible foam, which locally collapse before densifying to become a solid mass. This suggests that materials like sawdust can be very soft if not packed densely, which would also eliminate the porous (low density) characteristic of the sawdust that made it a desirable candidate to begin with. Sawdust from other types of wood could possibly yield more favorable results. Even though ground coffee is a porous and organic material similar in many ways to sawdust, it exhibited more of a typical material response, which includes an effective elastic regime followed by a plateau regime, under compression, suggesting that the coffee particles are much stiffer than those of sawdust, allowing the ground coffee to maintain its porosity under load.

Of the materials tested, ground coffee produced the most favorable combination of having a high strength-to-weight ratio in addition to large absolute strength. Hypotheses for why coffee performs so well include that the ground coffee has both significant surface roughness and irregular, jagged features that increase inter-particle friction. At the same time, releasing the vacuum pressure causes ground coffee to unjam relatively easily and flow well compared to many materials that have been tested qualitatively. The difference in the strength between the coarse and fine coffee grind can possibly be attributed to the coarse coffee having a larger size distribution of particles, as shown in FIGS. 8A-8F. When there is a larger range of particle sizes, smaller particles tend to fill the voids between larger ones to maximize the solid volume fraction, thereby minimizing the degrees of freedom of the particles to induce jamming.

It may be helpful to consider a concept from soil mechanics called the Uniformity Coefficient. The Uniformity Coefficient is the ratio of: the diameter grain (particle) of a size that is barely too large to pass through a sieve that allows 60 percent of the material (by weight) to pass through; to the diameter of a grain (particle) of a size that is barely too large to pass through a sieve that allows 10 percent of the material (by weight) to pass through. The resulting ratio is a measure of the degree of uniformity in a granular material, such as filter media. Another parameter of interest is sometimes called polydispersivity, which is the standard deviation of the cross sectional area of grains divided by the average cross sectional area of the grains. The polydispersivity of the coarsely ground coffee is 1.448. Thus, it is expected that material with a polydispersivity on the order of and having within its range 1.5 will be useful for a manipulator of the dimensions shown.

Another notable difference between ground coffee and the other materials tested is that ground coffee inherently contains some moisture (particularly in the form of an oil), which might contribute to the bulk strength due to attractive capillary forces between particles. It may also contribute lubrication in the unjammed state, increasing the medium's ability to flow. In general, thin layers of oil (nanometers thick) can greatly increase the friction angle of grains because of cohesion. As discussed above, a relatively larger friction angle for a granular medium gives rise to a relatively higher shear strength. For the manipulator applications discussed herein, relatively larger shear strengths are beneficial.

The tensile elements can be cables, belts, chains, wires, ropes, thread, filaments, etc. They can have periodic elements to aid in actuating, as in a chain, timing belt, etc.

The actuators can be rotational motors, linear actuators, shape memory alloys (which could also serve as tension elements), etc. Spooler motors have been used advantageously.

EXPERIMENTS

Two prototypes of a jammable manipulator have been tested. Representative components of both are illustrated with reference to FIG. 1 and FIG. 2. Both were composed of five serial jammable modules 104, 106a, 106b, 106c and 108. Each module used: coarsely ground coffee as the granular media 110, a low-stiffness compression spring 122 along its length, and an outer flexible membrane 110. The primary purpose of the spring was to help constrain the bending motion of each module to improve its precision while still being soft enough to maintain the overall flexibility of the manipulator. The springs also served as force-restoring elements to help return modules to a neutral position when unjammed. Any suitable spring with adequate force and shape restoration will work. For instance, a stiff foam can also be used.

Each module also included rigid end caps 112a, 112b for connecting one fluid line 144, 146a, 146b, 146c, 148 per module 106x, and for guiding the tension cables 120a, 120b, and one or two more, which ran along the length of the entire manipulator. All the fluid lines were connected to a single, off-board air vacuum pump 130. Each module's fluid line was also connected to an off-board assembly of solenoid valves 134, 136a, 136b, 136c, 138, shown in FIG. 1 to enable isolated jamming control of each module 106x. This allowed the manipulator to effectively achieve Z×Y DOFs, where Z is the number of modules and Y is the number of DOFs per module. Position control was performed by selectively jamming/unjamming individual modules 106x, as discussed above and controlling the length of the tension cables 120a, 120b.

As shown in FIG. 4, a first prototype of the manipulator was composed of five substantially identical modules 408, 406c 406b, 406a and 404. A significant challenge of designing the manipulator modules to resist loads in bending was to prevent grains from squeezing out of the mid-length portion of the modules, or where the modules tended to bend the most, because this is where the most strength is needed to support loads in the jammed state. A smooth-ridged, bellows-like outer membrane 410 (1.5 mm thick) was cast out of silicone to prevent the membranes from buckling during bending and to help maintain uniform distribution of the grains. The total length of the manipulator was 355 mm. The length of each module was 50 mm, and the narrowest and widest inner diameters of each module (due to the ridged bellows shape) was 20 mm and 30 mm, respectively. An 8 mm diameter spring with stiffness 600 N/m was implemented in each module.

This prototype demonstrated that jamming is very effective as a rapidly activatable tunable stiffness mechanism and that ground coffee provides adequate changes in stiffness to easily decouple not-jammed modules from jammed ones, as shown in FIG. 4. While this prototype exhibited high flexibility and could hold itself in complex shapes, it was barely strong enough to support its own weight when the entire manipulator was jammed in a horizontal position. The total mass of the manipulator was 190 grams. The mass percentage breakdown was: 23% end caps and springs, 36% silicone membranes, and 41% ground coffee. The mass of the tubes and tension cables was negligible.

A significant goal of the second prototype, as shown in FIGS. 3A-3F was to improve the strength-to-weight performance and payload capacity of the manipulator. The following changes were made: thin (150-microns thick) latex sheets—that were wrapped around and sealed—replaced the cast silicone membranes; the manipulator is tapered along its length, such that it's terminal module was narrower than its base module; and the springs had outer diameters equal to those of the modules in which they were contained. Commercially available springs were selected based on their relative dimensions (to maintain aspect ratios of individual modules and to create an overall tapered shape) and minimal stiffness. Because the membranes no longer had a confining structure built into them as the silicone membranes had, the larger-diameter springs served an additional purpose of maintaining the cross sectional area of each module during bending. A schematic of the manipulator is shown in FIG. 1.

The total length of the manipulator was 380 mm. Each module was designed to have a 2:1 length-to-diameter ratio. The modules were also designed to scale linearly to create the overall tapered shape. The stiffness of the springs 122 was approximately 180 N/m. The total mass of the manipulator was 345 grams (without electromechanical components). The mass percentage breakdown of the second prototype of the manipulator was: 43% end caps and springs, 7% latex membranes, and 50% ground coffee. By reducing the mass of the membranes, the relative mass of the ground coffee was increased, thereby increasing the robot's strength-to-weight ratio. However, the relative mass of the end caps and springs increased, not only because larger springs were used, but also because end cap design improved at the cost of becoming larger, to enable a more modular design than in the first prototype. A reasonable range for the diameter of each module would be from 10 mm to 1000 mm, and even more.

The second prototype could easily support its own weight when jammed in a horizontal position.

The system for the second prototype of the manipulator was complete with motors 118a, 118b (Dynamixel MX-28, available from Robotis—of Irvine, Calif.) for controlling the length of the cables 120a, 120b, and solenoid valves (not shown) (SMC NVKF334V, available from SMC Corporation of America-Noblesville, Ind.) for controlling the air flow at each module. While a manipulator composed of any number of modules requires only three sets of motors and cables, spaced 120° apart around the axis E of the manipulator, to control three DOFs (including compression/extension) of every module, and therefore create any arbitrary overall shape for the manipulator, four motors were employed, spaced 90° apart, to simplify the control.

A vacuum pump 130, with maximum 101.3 kPa (1 atm) vacuum pressure was used to jam the modules. A vacuum storage tank (not shown) was added in line with the pump to increase the short-term volumetric flow rate of air.

The disclosed manipulator has unique capabilities. The results presented here are from tests performed with the second prototype of the manipulator shown in FIG. 1 and FIGS. 3A-3F.

A speed parameter of interest is the time it takes for the manipulator to transition between jammed and not-jammed states, since this influences the manipulator bandwidth and its ability to respond to its environment.

Tests for determining the jamming speed of the manipulator were conducted by holding the manipulator, (with one fixed end) in a fully not-jammed, straight, horizontal position and dropping the free end of the manipulator. The time between when the solenoid valves were activated and when the manipulator jammed and reached a completely rigid and still position was determined. Because the transition time was rapid, this was done by recording a video of the test and determining the speed by parsing individual video frames. The time required to jam the manipulator was 0.2 seconds. This time can vary for a given system depending on the volumetric flow rate of the fluid, which in this case was air. Similar tests were conducted to determine the unjamming speed, which was 0.1 seconds.

Many manipulator applications require a system to pick up and transport payloads, thus requiring adequate strength from the jammable modules. As previously discussed, there is potential to further understand how grain properties affect jamming to enable designers and engineers to specify grain properties to fulfill functional requirements for a given application. In general, even jammed granular media that can support high compression loads have minimal tensile strength; for a vacuumed system, the tensile strength is expected to be dictated by the applied vacuum pressure because grains typically do not interlock to resist tensile loads. Therefore, the bending strength of jammed systems is expected to be limited by the differential jamming pressure.

An important advantage of the manipulator system presented here is that the cables can provide significant tensile force. Tests were done to determine the stiffness and strength of the jammed manipulator with and without the use of tension cables. In these tests, the manipulator was cantilevered in the jammed configuration and weights were hung from its free end, and the displacement of the tip was recorded. Both cases appeared to have both an effective linear elastic regime and a yield point. Without tension cables, the yield load was 80 grams; with tension cables, the yield load was 740 grams. This latter result indicates that the manipulator was able to support a payload equal to more than 200% of its own weight (without electromechanical components); in contrast, many industrial manipulators can support payloads that are only a fraction of their own weigh.

When the tension cables were not utilized, the failure mode that was observed—when adding payload to the free end of the jammed, horizontal manipulator—was the jammed grains separating from the smooth, rigid end caps. This effect can be mitigated by roughening or adding protruding features to the end plates.

A very impressive advantage that the jammable manipulator has over traditional systems is its flexibility and ability to conform to its environment with simple control. For example, the manipulator can easily wrap around an obstacle because the not-jammed modules can passively conform to other objects, like a bean-bag laid upon them. This contrasts with a more traditional system in which high local precision (usually via motors) is required for complex maneuvering. In addition, because of the high DOFs of the system, the manipulator can reach the same end effector position with many configurations.

Figure 3A:
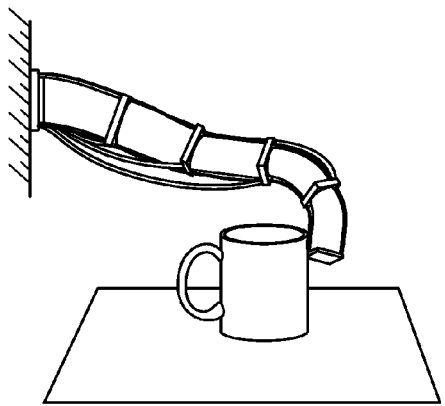
FIGS. 3A, 3B, 3C, 3D, 3E and 3F show, schematically, different configurations in which a representative, tapered diameter embodiment of an apparatus invention hereof can be held, showing it highly extended (FIG. 3B) extremely bent back upon itself (FIG. 3C) and curled into various shapes (FIGS. 3A, 3E and 3F)
Figure 3B:
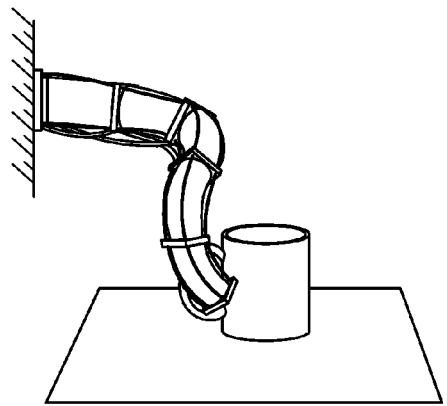
Figure 3C:
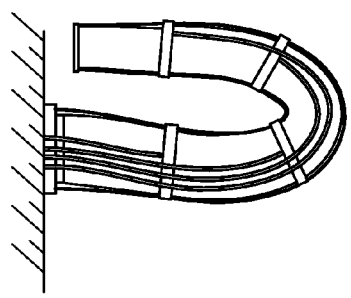
Figure 3D:
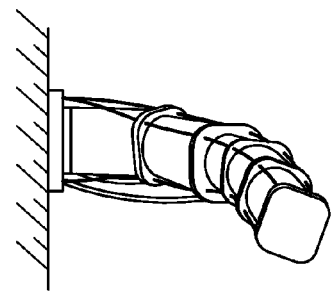
Figure 3E:
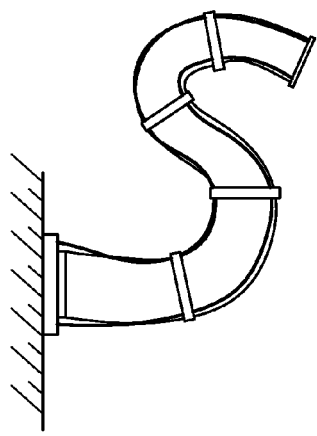
Figure 3F:
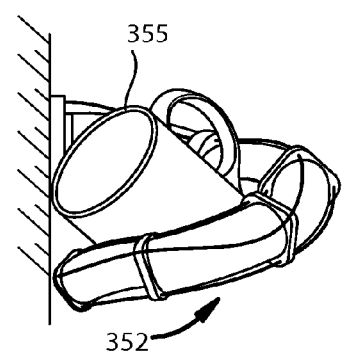

FIG. 3C demonstrates how a manipulator is able to fold on itself and maintain highly articulated configurations via jamming. The reachable workspace boundary of the manipulator is a squashed sphere with a radius on one hemisphere equal to the manipulator length, and slightly less (for one embodiment, ⅘ the manipulator length) on the squashed side, as shown schematically with reference to FIG. 11, discussed above. The flexibility of the manipulator also depends on details such as the stiffness of the spring and membrane; the first prototype, shown in FIG. 4, was more compliant than the second one, shown in FIG. 3A-3F due to their different components. A highly articulated and adaptable manipulator such as the one presented would also benefit human-safe robots, as such robots can be more responsive and accommodating to their environments.

As previously discussed, the strength of the manipulator can be further improved by providing end caps different from those shown. The relatively large, rigid end caps can be removed altogether, such as shown in FIG. 1, and the plumbing can be integrated more seamlessly into the manipulator, such as by running the tubes through the center of the structure.

One limitation of using vacuum pressure as the jamming mechanism is that the maximum differential jamming pressure is atmospheric pressure. Therefore, utilizing positive pressure can significantly increase the strength of jammed granular systems.

Positive pressure may be easily provided to each module individually, because the pump that establishes vacuum pressure may also establish positive pressure. Positive pressure can be used to aid unjamming a jammed module, especially with media that tends to clump or adhere to itself for various reasons. For instance, a puff of positive pressure may be applied to just jostle the grains from their slightly adhered state when jammed. Positive pressure may also be used as an adjunct to the tensile elements, to contribute to positioning or conforming the manipulator, inflating one or more module as a balloon, which also has a certain amount of rigidity. In fact, some modules may be dedicated to being inflated, and their envelope may be specially provided to withstand the inflating pressures, and to provide structural integrity.

To simplify the manipulation capabilities of the manipulator, a rotational degree of freedom can be added to the robot (e.g., by adding another motor at the base of the manipulator) to rotate the entire structure 102. Or, rather than a motor, a simple swivel may be provided, for passive rotation by another agency. Because it is at the base, such an additional actuator would not add to the mass or bulk or complexity of the extended part of the manipulator.

This new type of manipulator architecture in which binary local control is coupled with global actuation creates new and interesting problems for motion and path planning of manipulators. Important cost objectives are introduced, such as the number of operations that are required to reach an end effector position. Additionally, the mechanical compliance of granular systems adds to the complexity of the problem. It is possible to use visual tracking systems, such as through infrared cameras, to provide closed-loop feedback for controlling manipulator position. It is also possible to mimic manipulator-like systems in nature, such as elephant trunks and cephalopod (octopi and squid) tentacles. For example, octopi create pseudo discrete joints along their flexible tentacles to efficiently grasp nearby food.

It is also possible to integrate sensors along the manipulator, to not only determine the shape and position of the manipulator but to also sense its environment. For instance, force feedback can be established by providing force/torque sensors in each end cap, between each pair of modules.

The foregoing has discussed using a serially jammable manipulator as a conventional robotic manipulator, itself acting as a manipulating effector by assuming a variety of shapes, as illustrated, or by carrying an end effector or other instrumentation. Such manipulators can also be used for all manner of tasks such as are accomplished by elongated scopes and tools for entering a patient's body, either with an end effector, or without. This includes endoscopes, proctoscopes, various scopes for examining and administering care or treatment to oral, esophageal and vaginal structures, such as the cervix, uterus, vaginal vestibule, etc. A jammable manipulator can be made soft and not-jammed almost instantly (as discussed above, on the order of 0.1 sec), so that the comfort of the patient may be enhanced and safeguarded. Or, conversely, they can be inserted and then gently stiffened by jamming, also to enhance the patient's comfort.

Such a jammable vaginal instrument may be used for treatment, such as performing surgical procedures, drug or topical medicine delivery. They may be used for observation, to visually inspect internal structures, or to observe by gentle and precise placement of instrumentation. Such an instrument may also be used for artificial insemination, as well as instruction as to effective sexual techniques and practices. With or without force feedback capabilities, such an instrument can be used to diagnose sexual dysfunction, and instruct and demonstrate constructive and positive sexual functions. They may also be used to instruct patients in achieving pleasurable, proper and supportive sexual activities, and even to provide such activities.

In summary, primary advantages that the disclosed system have over existing methods are that the jammable manipulator has the potential to: achieve more complex configurations due to its increased flexibility; be more robust due to its simple construction and absence of electromechanical components along the actual manipulator arm; be less expensive to manufacture due to its simple construction and small number of electromechanical components (traditional actuators) required; have a high payload-to-weight ratio; and quickly respond to human counterparts.

The foregoing has discussed media that is jammable via application of a vacuum to a sealed envelope within which the jammable media resides. Other techniques for jamming are viable and can be arranged as serial continuum of jammable modules with tensile members disclosed herewith. Such other jammable media are described in some detail in U.S. patent application Ser. No. 553,971, filed on Sep. 3, 2009, published as publication no. 20100054903 on Mar. 4, 2010, entitled, Method and Device for Manipulating and Object, the full content of which is fully incorporated herein by reference. The '971 patent discusses an end effector that is activated with jammable material.

The jammable media is referred in the '971 application as phase change material, because jammable material is, in fact, a specific form of material that changes from a solid-like condition to a flowable, liquid-like condition, by jamming. The inventions disclosed herein can and are intended to be used with all suitable jammable materials, as well as suitable phase change materials. What is important is that there be a relatively large change in strength between the two phases, e.g. jammed and not jammed, as well as a small activation speed. The large change in strength is required so that when the cables are pulled, only the desired segments (e.g., not-jammed) deform while the others (jammed) do not). For instance, electrorheological (ER) fluids and magnetorheological (MR) fluids used alone typically do not work as well as jamming using vacuum, because they do not achieve a large enough change in strength and their absolute strength in the phase analogous to a solid is most likely not large enough to do useful tasks in many applications. However, with those considerations in mind, such phase change materials can be used, if they meet the other criteria.

A material that has a temperature-controlled stiffness, such as melting/cooling wax, can result in very large changes in strength, and such a material could be used with inventions hereof. To some extent, cycle speed may be an impediment to using temperature controlled phase change media. Additional accelerating components can be used, such as Peltier cooling plates, etc. The following discussion is taken in part from the '971 patent application.

Other phase change materials can be used. One such material is a dilatant material such as a combination of cornstarch and water, which can be activated to a more solid state via application of vibration. A dilatant (also called shear thickening) material is one in which viscosity increases with the rate of shear. The dilatant effect is believed to occur when closely-packed particles are combined with enough liquid to fill the gaps between them. At low velocities, the liquid acts as a lubricant, and the dilatant flows easily. At higher velocities, the liquid is unable to fill the gaps created between particles, and friction greatly increases, causing an increase in viscosity.

Other materials that are not truly phase change materials, but which are contemplated for use in a manipulator in accordance with certain embodiments of the present teachings, can include electrorheological (ER) fluids and magnetorheological (MR) fluids. ER fluids are suspensions of extremely fine non-conducting particles (up to, for example, 50 micrometers in diameter) in an electrically insulating fluid. The apparent viscosity of these fluids can change reversibly by an order of up to 100,000 in response to an electrical field. An MR fluid is a suspension of micrometer-sized magnetic particles in a carrier fluid, usually a type of oil. When subjected to a magnetic field, the fluid greatly increases its viscosity, to the point of becoming a viscoelastic solid. The yield stress of the fluid when in its active (on) state can be controlled very accurately by varying the magnetic field intensity.

Yet another phase change material can include supersaturated sodium acetate solutions that, when heated to around 100 degree C. and subsequently allowed to cool, become supersaturated. This solution is capable of supercooling to room temperature without forming crystals and then, by application of a small amount of energy such as a mechanical shock, a nucleation center is formed and causes the solution to crystallize into a solid sodium acetate trihydrate. This solidification is reversible through application of heat.

Some of the materials referred to herein may be considered by certain people of skill in the art not truly undergo a phase change. Thus, the term phase change materials as used herein includes material, as described herein and as would be appreciated by those skilled in the art, which behaves as if it undergoes a phase change.

Devices used to actuate the jamming or other phase change material within the envelope will vary based on the type of phase change material and its mode of activation. For jamming materials that exhibit change from a solid-like state to a free-flowing state (and vise versa) based on a volume change (e.g., ground coffee), the actuation device can comprise, for example, a mechanical pump mechanism.

For activating dilatant material, a low voltage, low current miniature vibrating motor can be utilized. The vibrating motor can, for example, operate on a 1-5 VDC motor with an offset weighted shaft, such as those used in cell phones and pagers for a vibrating alert signal. Electrical plates, for example one inside of the envelope and one outside of the envelope, can be used to activate ER material. Magnets located in or near the envelope can be used to activate MR material by creating a magnetic field within the housing.

While particular embodiments have been shown and described, it will be understood by those skilled in the art that various changes and modifications may be made without departing from the disclosure in its broader aspects. It is intended that all matter contained in the above description and shown in the accompanying drawings shall be interpreted as illustrative and not in a limiting sense.

Important aspects of inventions hereof are to use a phase change material contained within at least one module, with at least one tensile element and one actuator. More than one tensile element and actuator can be used, as described. More than one module can be so actuated. The phase change material can be a jammable material, such as a granular material, of which ground coffee is exemplary. With a jammable phase change material, the envelope is impermeable to a working fluid suitable for jamming and unjamming the jammable material. For other phase change materials, the envelope must be impervious to degradation by the conditions and materials that bring about the phase change, such as heat, magnetic and electric fields, etc.

Manipulators as disclosed may be used for a variety of medical devices, including those for entry into a natural body opening, such as endoscopes, proctoscopes, intra-vaginal devices, naso-gastric devices, feeding tubes and devices. They can be used with devices for entering a surgically created opening, such as laparoscopic surgical tools, or as the laparoscopically insertable tool itself. They can be used for inspecting and repairing and maintaining pipes, conduits and other constricted mechanical geometries.

This disclosure describes and discloses more than one invention. The inventions are set forth in the claims of this and related documents, not only as filed, but also as developed during prosecution of any patent application based on this disclosure. The inventors intend to claim all of the various inventions to the limits permitted by the prior art, as it is subsequently determined to be. No feature described herein is essential to each invention disclosed herein. Thus, the inventors intend that no features described herein, but not claimed in any particular claim of any patent based on this disclosure, should be incorporated into any such claim.

Some assemblies of hardware, or groups of steps, are referred to herein as an invention. However, this is not an admission that any such assemblies or groups are necessarily patentably distinct inventions, particularly as contemplated by laws and regulations regarding the number of inventions that will be examined in one patent application, or unity of invention. It is intended to be a short way of saying an embodiment of an invention.

An abstract is submitted herewith. It is emphasized that this abstract is being provided to comply with the rule requiring an abstract that will allow examiners and other searchers to quickly ascertain the subject matter of the technical disclosure. It is submitted with the understanding that it will not be used to interpret or limit the scope or meaning of the claims, as promised by the Patent Office's rule.

The foregoing discussion should be understood as illustrative and should not be considered to be limiting in any sense. While the inventions have been particularly shown and described with references to preferred embodiments thereof, it will be understood by those skilled in the art that various changes in form and details may be made therein without departing from the spirit and scope of the inventions as defined by the claims.

The corresponding structures, materials, acts and equivalents of all means or step plus function elements in the claims below are intended to include any structure, material, or acts for performing the functions in combination with other claimed elements as specifically claimed.

Aspects of Inventions

The following aspects of inventions hereof are intended to be described herein, and this section is to ensure that they are mentioned. They are styled as aspects, and although they appear similar to claims, they are not claims. However, at some point in the future, the applicants reserve the right to claim any and all of these aspects in this and any related applications.

A-1. A manipulator comprising:
a. at least one module, each module comprising:
  i. a basal end and a terminal end;
  ii. an envelope;
  iii. within the envelope, a jammable media capable of reversibly changing from a jammed, state to a not-jammed, state; and
  iv. coupled with each envelope a jamming actuator, arranged to reversibly establish a jammed and a not-jammed state of the jammable media;
b. at least one tensile member extending from the basal end to the terminal end; and
c. coupled to each at least one tensile member, an actuator, arranged to provide a variable tension to the tensile member.

A-2. The manipulator of aspect 1, the at least one module comprising at least two modules, arranged serially, from a basal end to a terminal end.

A-3. The manipulator of aspects 1-2, the jammable media having a jammed, solid-like phase when subjected to a pressure differential of a working fluid, and a not-jammed, liquid-like phase when not subjected to a pressure differential, the envelope being impermeable to the working fluid, the jamming actuator comprising a pressure source, arranged to reversibly establish within the envelope a fluid pressure that is less than ambient pressure outside the envelope and a pressure that is at least equal to the ambient pressure.

A-4. The manipulator of any of aspects 1-3, the jammable media comprising a granular media.

A-5. The manipulator of any of aspects 2-4, one of the at least two modules comprising a base module, which is adjacent to only one other module, and the other of the at least two modules comprising a terminal module, which is adjacent to only one other module.

A-6. The manipulator of any of aspects 1-5, each envelope comprising a flexible elastic material.

A-7. The manipulator of any of aspects 3-5, the pressure source comprising a vacuum source.

A-8. The manipulator of any of the foregoing aspects, the at least one tensile members comprising at least two tensile members.

A-9. The manipulator of aspect 8, the at least two tensile members spaced equally around the manipulator perimeter.

A-10. The manipulator of any of aspects 8 and 9, the at least two tensile members arranged to twist along the length of the manipulator.

A-11. The manipulator of aspect 10, the at least two tensile members arranged to twist with opposite chiralities.

A-12. The manipulator of any of aspects 1-7, the at least one tensile members comprising three tensile members.

A-13. The manipulator of any of aspects 1-7, the at least one tensile members comprising four tensile members.

A-14. The manipulator of any of the foregoing aspects, further comprising, for each module, a compression spring that extends substantially parallel with the at least one tensile members.

A-15. The manipulator of aspect 14, each envelope having a cross-sectional dimension with a perimeter, each compression spring having a perimeter that is substantially congruent with the perimeter of the envelope.

A-16. The manipulator of aspect 15, the compression spring comprising a spiral spring.

A-17. The manipulator of any of the foregoing aspects, the at least one tensile members comprising a cable.

A-18. The manipulator of any of the foregoing aspects, the at least one actuators comprising a spooler motor.

A-19. The manipulator of aspect 4, the granular media comprising ground coffee.

A-20. The manipulator of aspect 19, the coffee having a particle distribution of between about 300 microns and about 2000 microns.

A-21. The manipulator of aspect 19, the coffee including natural coffee oil.

A-22. The manipulator of any of aspects 4 and 19-21, the granular material having a relatively high friction angle A-23. The manipulator of any of aspects 4 and 19-22, the granular media comprising a grain size distribution that ranges from relatively large to relatively small grains within the range.

A-24. The manipulator of any of aspects 4 and 19-23, the granular media comprising media having a polydispersivity index on the order of approximately 1.5.

A-25. The manipulator of any of aspects 4 and 19-24, the granular media comprising grains of predominantly an elongated irregular shape.

A-26. The manipulator of any of aspects 4 and 19-25, the granular media comprising grains which, in a jammed state, provide relatively high strength and, in a not-jammed state, flow relatively easily.

A-27. The manipulator of any of aspects 4 and 19-26, the granular media comprising grains which in a jammed state, provide relatively high friction angle and, in a not jammed-state, provide a relatively low friction angle.

A-28. The manipulator of any of aspects 3, 4, 7 and 9-27, the pressure source having a cycle speed of less than 0.2 seconds.

A-29. The manipulator of any of aspects 3, 4, 7 and 9-28, the pressure source capable of maintaining the pressure within the envelope at substantially any pressure between atmospheric and essentially zero psi.

A-30. The manipulator of any of the foregoing aspects, further comprising an end effecter.

A-31. The manipulator of any of aspects 2-30, further comprising, extending along the length of at least two of the at least two modules, within each respective envelope, a lumen.

A-32. The manipulator of aspect 31, the lumen extending along the center of each respective envelope.

A-33. The manipulator of any of the foregoing aspects, the modules having a diameter of between approximately 10 mm and 100 mm.

A-34. The manipulator of any of the foregoing aspects, the modules having a length to diameter ratio of approximately 2:1.

A-35. The manipulator of any of the foregoing aspects, further configured as an endoscope A-36. The manipulator of any of the foregoing aspects, further configured as a proctoscope.

A-37. The manipulator of any of the foregoing aspects, further configured as an intravaginal device.

A-38. The manipulator of any of the foregoing aspects, further configured as a nasogastric device.

A-39. The manipulator of any of the foregoing aspects, further configured a feeding device.

A-40. The manipulator of any of the foregoing aspects, further configured as a laparoscopic device.

A-41. The manipulator of aspect 1 and any of the foregoing aspects 2, 3, 5, 31 and any aspect that depends therefrom, further comprising releasable joints between adjacent modules, so as to be modularly separable.

A-42. The manipulator of aspect 2, 3, 5, 31 and any aspect that depends therefrom, further comprising, between each adjacent pair of modules, a linking joint.

A-43. The manipulator of aspect 42, further comprising a base, to which is attached the base module.

A-44. The manipulator of aspect 42, further comprising an end cap, which is attached to the second end of the terminal module.

A-45. A manipulator comprising:
  a. at least one module, each module comprising:
    i. a basal end and a terminal end;
    ii. an envelope;
    iii. within the envelope, a phase change media capable of reversibly changing from a solid-like phase to a liquid-like phase; and
    iv. coupled with each envelope a phase change actuator, arranged to reversibly establish phase change of the phase change media;
  b. at least two tensile members extending from the basal end to the terminal end; and
  c. coupled to each at least two tensile members, an actuator, arranged to provide a variable tension to the tensile member.

A-46. The manipulator of aspect 45, the at least two tensile members spaced equally around the manipulator perimeter.

A-47. The manipulator of aspect 46, the at least two tensile members arranged to twist along the length of the manipulator.

A-48. The manipulator of aspect 47, the at least two tensile members arranged to twist with opposite chiralities.

A-49. The manipulator of any of the foregoing aspects, further comprising a second manipulator as claimed in aspect 1.

A-50. A method for positioning a continuum style manipulator having at least one module having an envelope containing jammable media and at least one one tensile member extending along the module, the method comprising:
  a. establishing in the jammable media of at least a first module, a not-jammed state;
  b. positioning the first module in a desired position;
  c. establishing in the jammable media of the positioned first module, a jammed state;
  d. continuing with all remaining modules to establish in each as yet not positioned module, a not-jammed state, and then positioning the remaining modules in a desired position, and then establishing in the jammable media of the positioned remaining modules, a jammed state.

A-51. The method of aspect 50, wherein the step of continuing with all remaining modules to establish in each as yet not positioned module, a not-jammed state, and then positioning the remaining modules in a desired position, and then establishing in the jammable media of the positioned remaining modules, a jammed state is conducted by establishing a jammed state in only one positioned, not-jammed module, at a time.

A-52. The method of aspect 50, wherein the step of continuing with all remaining modules to establish in each as yet not positioned module, a not-jammed state, and then positioning the remaining modules in a desired position, and then establishing in the jammable media of the positioned remaining modules, a jammed state is conducted by establishing a jammed state in more than one positioned, not-jammed module, at the same time.

Having described the invention, what is claimed is:
1. A manipulator comprising:
  a. at least one module, each module comprising:
    i. a basal end and a terminal end;
    ii. an envelope;

iii. within the envelope, a media capable of reversibly changing from a solid-like phase to a liquid-like phase;

iv. coupled with each envelope, a phase change actuator, arranged to reversibly establish phase change of the media;

b. at least two tensile members extending from the basal end to the terminal end; and c. coupled to each tensile member, a tensile actuator, each tensile actuator arranged to provide a variable tension to the respective tensile member.

2. The manipulator of claim 1, comprising at least two modules, arranged serially, from a basal end to a terminal end.

3. The manipulator of claim 1, the media comprising a jammable media.

4. The manipulator of claim 3, the jammable media having a jammed, solid-like phase when subjected to a pressure differential of a working fluid, and a not-jammed, liquid-like phase when not subjected to a pressure differential, the envelope being impermeable to the working fluid, the phase change actuator comprising a pressure source, arranged to reversibly establish within the envelope a fluid pressure that is less than ambient pressure outside the envelope and a pressure that is at least equal to ambient pressure.

5. The manipulator of claim 1, the solid-like phase exhibiting a yield stress and the liquid like phase exhibiting, at most, a negligible yield stress.

6. The manipulator of claim 1, the at least two tensile members spaced equally around the manipulator perimeter.

7. The manipulator of claim 6, the at least two tensile members arranged to twist along the length of the manipulator.

8. The manipulator of claim 7, the at least two tensile members arranged to twist with opposite chiralities.

9. The manipulator of claim 1, the at least two tensile members comprising three tensile members.

10. The manipulator of claim 1, the at least two tensile members comprising four tensile members.

11. The manipulator of claim 1, further comprising, for each module, an anti-buckling element that extends substantially parallel with the at least two tensile members.

12. The manipulator of claim 11, each envelope having a cross-sectional dimension with a perimeter, each anti-buckling element having a perimeter that is substantially congruent with the perimeter of the envelope.

13. The manipulator of claim 11, the anti-buckling element comprising a compression spring.

14. The manipulator of claim 1, each at least two tensile members comprising a cable.

15. The manipulator of claim 3, the jammable material comprising granular material.

16. The manipulator of claim 3, the jammable material comprising granular media comprising a grain size distribution that ranges from relatively small grains to larger grains approximately 20/3 times the size of the relative small grains within the range.

17. The manipulator of claim 3, the jammable media comprising granular media comprising media having a polydispersivity index on the order of approximately 1.5.

18. The manipulator of claim 3, the jammable media comprising granular media comprising grains of predominantly irregular shapes.

19. The manipulator of claim 3, the jammable media comprising granular media comprising grains which, in a jammed state, provide relatively high friction angle and, in a not jammed-state, provide a relatively low friction angle.

20. The manipulator of claim 4, the pressure source having a cycle speed of less than 0.2 seconds.

21. The manipulator of claim 1, further comprising an end effecter.

22. The manipulator of claim 1, further comprising, extending along the length of at least two of the at least one module, within each respective envelope, a lumen.

23. The manipulator of claim 1, the modules having a length to diameter ratio of approximately 2:1.

24. The manipulator of claim 1, further configured as an endoscope.

25. The manipulator of claim 1, further configured as a proctoscope.

26. The manipulator of claim 1, further configured as an intravaginal device.

27. The manipulator of claim 1, further configured as a nasogastric device.

28. The manipulator of claim 1, further configured a feeding device.

29. The manipulator of claim 1, further configured as a laparoscopic device.

30. The manipulator of claim 2, further comprising a releasable joint between adjacent modules, so as to be modularly separable.

31. The manipulator of claim 1, further comprising a sheath that surrounds the at least one module and the at least one tensile member.

32. A manipulator comprising:
a. at least one module, each module comprising:
i. a basal end and a terminal end;
ii. an envelope;
iii. within the envelope, a jammable media capable of reversibly changing from a jammed, state to a not-jammed, state; and
iv. coupled with each envelope a jamming actuator, arranged to reversibly establish a jammed and a not-jammed state of the jammable media;
b. at least two tensile members extending from the basal end to the terminal end; and
c. coupled to each at least two tensile members, a tensile actuator, each tensile actuator arranged to provide a variable tension to the tensile member.

33. A method for positioning a continuum style manipulator having at least one module having an envelope containing jammable media and at least one tensile member extending along the module, the method comprising:
a. establishing in the jammable media of at least a first module, a not-jammed state;
b. positioning the first module in a desired position;
c. establishing in the jammable media of the positioned first module, a jammed state;
d. continuing with all remaining modules to establish in each as yet not positioned module, a not-jammed state, and then positioning the remaining modules in a desired position, and then establishing in the jammable media of the positioned remaining modules, a jammed state.

34. The method of claim 33, wherein the step of continuing with all remaining modules to establish in each as yet not positioned module, a not-jammed state, and then positioning the remaining modules in a desired position, and then establishing in the jammable media of the positioned remaining modules, a jammed state is conducted by establishing a jammed state in only one positioned, not-jammed module, at a time.

\* \* \* \* \*